United States Patent
Hanson et al.

(10) Patent No.: US 12,226,637 B2
(45) Date of Patent: Feb. 18, 2025

(54) CONNECTION MECHANISM FOR THIN FILM STIMULATION LEADS

(71) Applicant: Cirtec Medical Corporation, Brooklyn Park, MN (US)

(72) Inventors: Todd Hanson, Brooklyn Park, MN (US); Norbert Kaula, Brooklyn Park, MN (US); Daniel Oster, Brooklyn Park, MN (US); Alanna Hentges, Brooklyn Park, MN (US); Johnny Khith, Brooklyn Park, MN (US); Jeremy Lug, Brooklyn Park, MN (US); Angelo Fruci, Brooklyn Park, MN (US); Angel Oudomrak, Brooklyn Park, MN (US)

(73) Assignee: Cirtec Medical Corporation, Brooklyn Park, MN (US)

( * ) Notice: Subject to any disclaimer, the term of this patent is extended or adjusted under 35 U.S.C. 154(b) by 882 days.

(21) Appl. No.: 17/212,283

(22) Filed: Mar. 25, 2021

(65) Prior Publication Data
US 2021/0299451 A1    Sep. 30, 2021

Related U.S. Application Data

(60) Provisional application No. 63/002,857, filed on Mar. 31, 2020.

(51) Int. Cl.
*A61N 1/36*    (2006.01)
*A61N 1/05*    (2006.01)

(52) U.S. Cl.
CPC ....... *A61N 1/36125* (2013.01); *A61N 1/0553* (2013.01)

(58) Field of Classification Search
CPC .............. A61N 1/36125; A61N 1/0553; A61N 1/0556; A61N 1/048
See application file for complete search history.

(56) References Cited

U.S. PATENT DOCUMENTS

| | | | | |
|---|---|---|---|---|
| 3,581,736 A | * | 6/1971 | Zenkich | .................... A61B 5/25 600/394 |
| 3,750,094 A | * | 7/1973 | Zenkich | ................. A61B 5/273 600/394 |

(Continued)

OTHER PUBLICATIONS

"Substrate." Vocabulary.com Dictionary, Vocabulary.com, https://www.vocabulary.com/dictionary/substrate. Accessed Feb. 5, 2024. (Year: 2024).*

(Continued)

*Primary Examiner* — Lynsey C Eiseman
*Assistant Examiner* — Christopher J Mutchler
(74) *Attorney, Agent, or Firm* — Haynes and Boone, LLP

(57) ABSTRACT

A lead assembly includes a thin film body supporting a plurality of electrodes configured to provide electrical stimulation or sensing. The thin film body includes a substrate. A plurality of electrode connection traces is situated on the thin film body and electrically connected to respective ones of the plurality of electrodes. A connection wire is configured to provide stimulation or sensing signals for transmission to the plurality of electrodes. The connection wire extends from a lead and is substantially larger than each of the electrode connection traces. A coupling structure is configured to provide electrical connection between the connection wire and the electrode connection traces.

20 Claims, 25 Drawing Sheets

(56) References Cited

U.S. PATENT DOCUMENTS

| | | | | |
|---|---|---|---|---|
| 3,964,470 | A * | 6/1976 | Trombley | A61N 1/05 600/377 |
| 4,207,904 | A * | 6/1980 | Greene | A61N 1/0492 607/152 |
| 7,787,959 | B1 * | 8/2010 | Morgan | B82Y 30/00 607/116 |
| 8,123,576 | B2 * | 2/2012 | Kim | A61B 5/274 600/394 |
| 9,211,400 | B2 * | 12/2015 | Bachinski | A61N 1/30 |
| 10,349,853 | B2 * | 7/2019 | Su | A61B 5/05 |
| 11,672,487 | B2 * | 6/2023 | Cantwell | A61B 5/24 600/377 |
| 2008/0140152 | A1 * | 6/2008 | Imran | A61N 1/0556 607/46 |
| 2012/0167385 | A1 * | 7/2012 | McGiboney | A61N 1/3752 29/846 |
| 2016/0045723 | A1 * | 2/2016 | Bornzin | A61N 1/37514 607/45 |
| 2016/0074650 | A1 * | 3/2016 | De Kock | A61N 1/0553 607/116 |
| 2016/0331326 | A1 * | 11/2016 | Xiang | A61B 5/24 |
| 2019/0336771 | A1 * | 11/2019 | Voit | A61N 1/36062 |

OTHER PUBLICATIONS

Quality Crimping Handbook (PDF). Molex Application Tooling Group. 1996. (Year: 1996).*

* cited by examiner

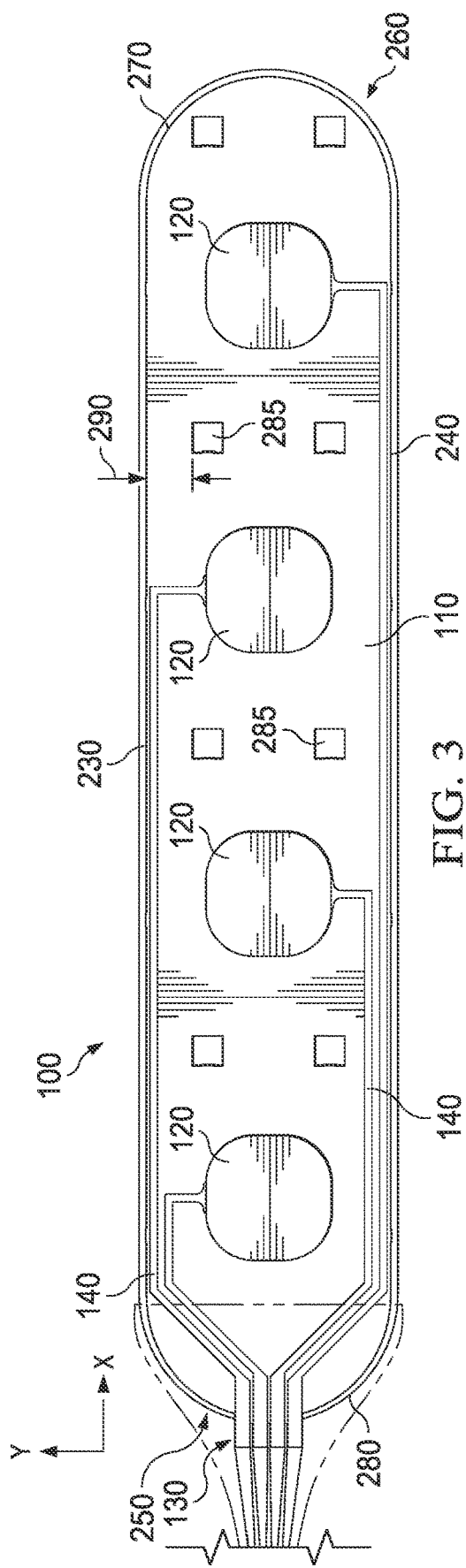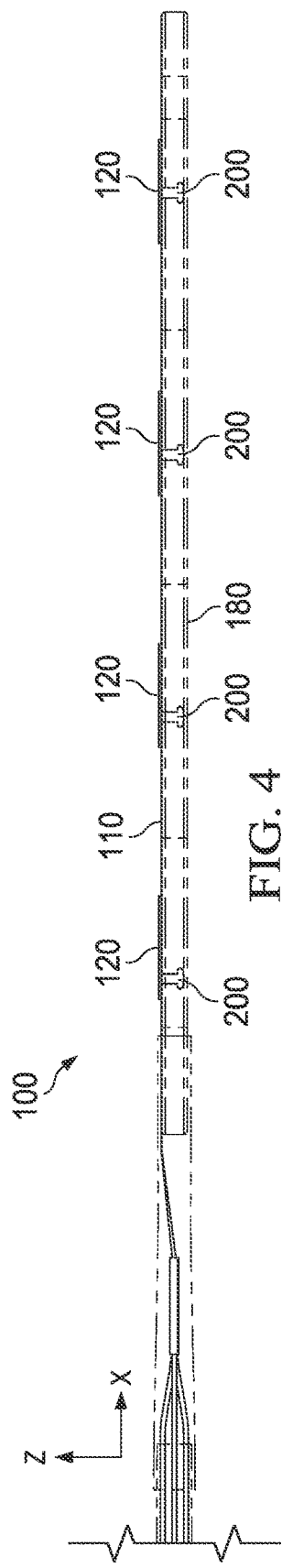

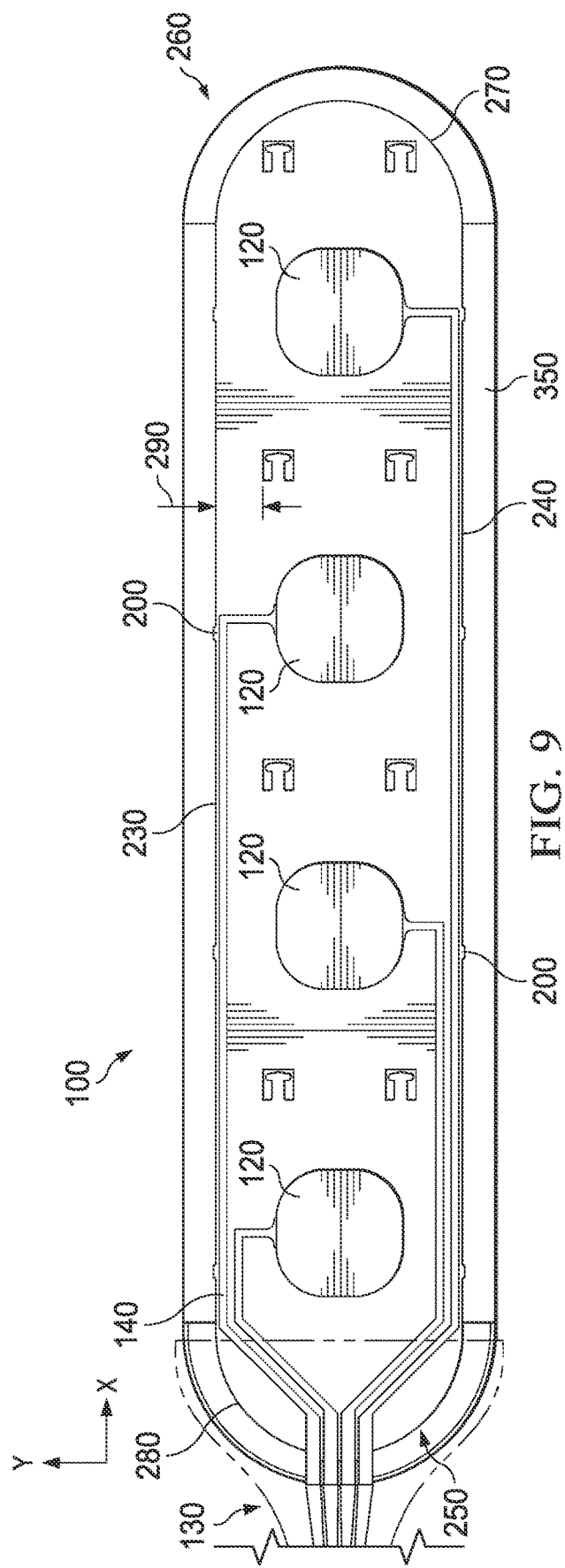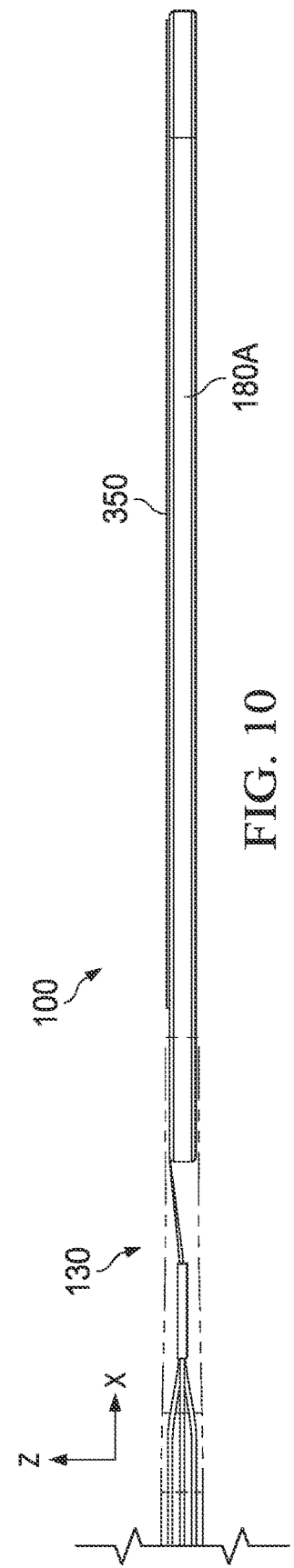
FIG. 9
FIG. 10

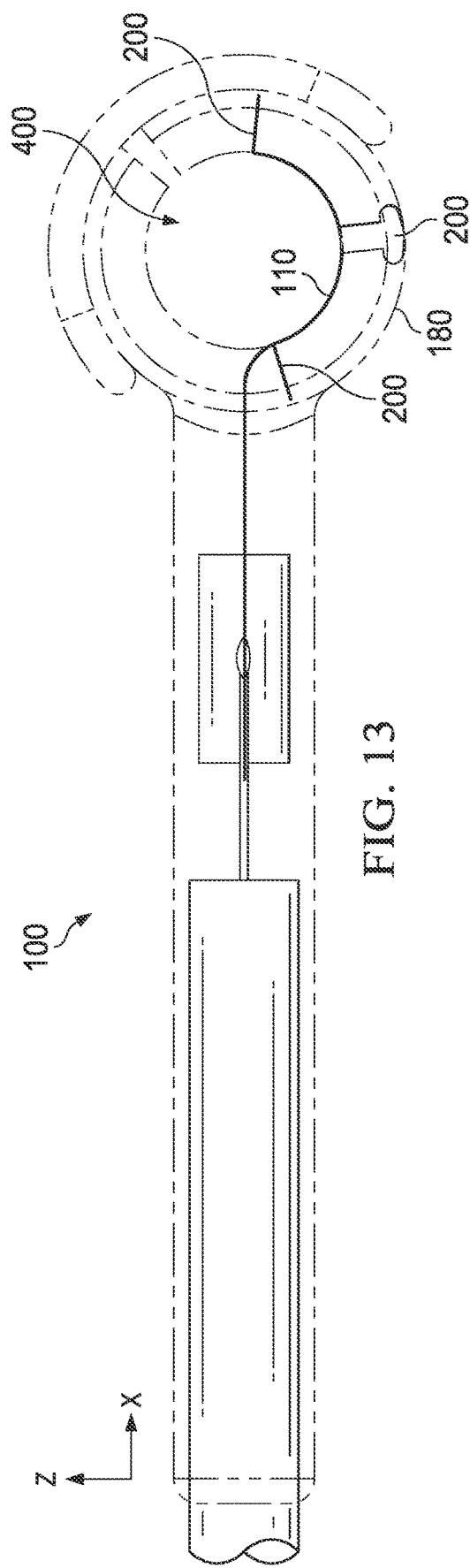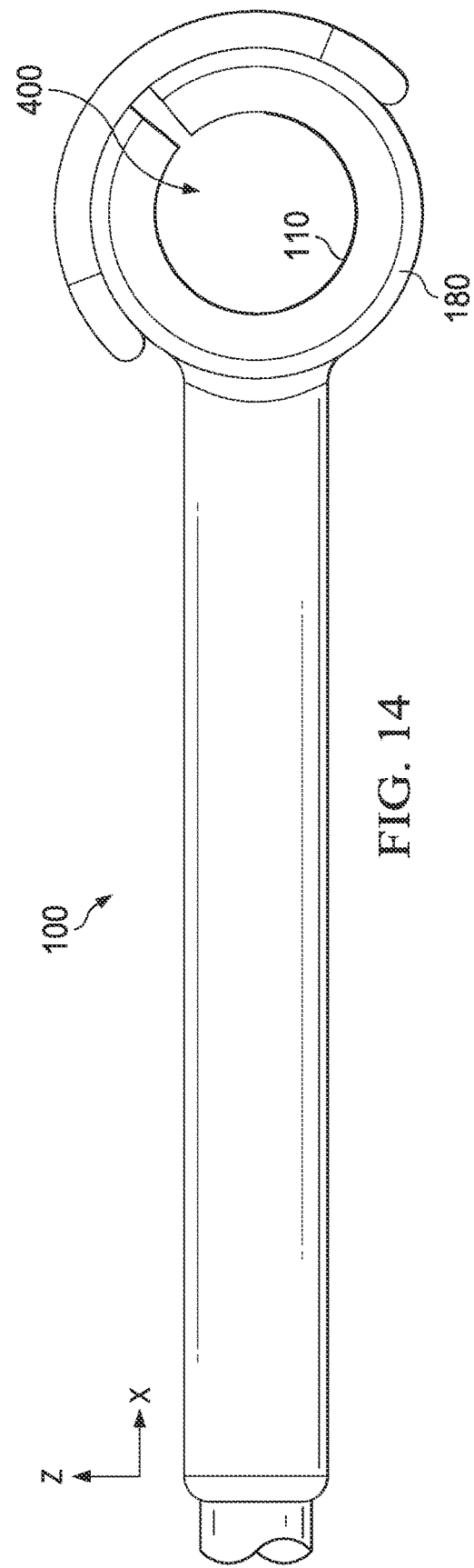

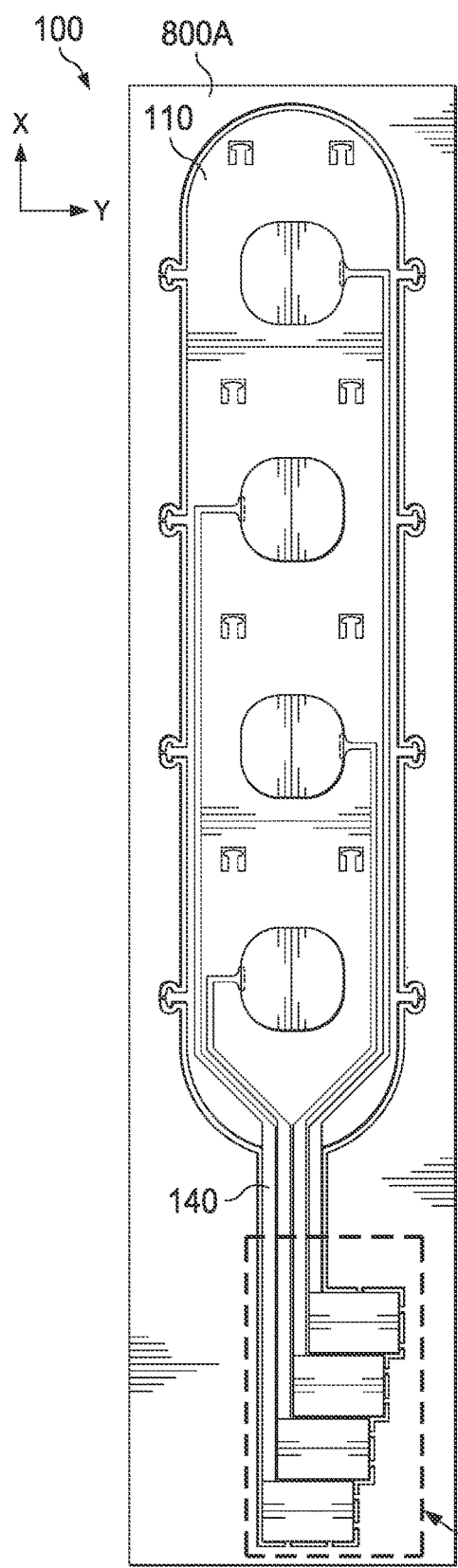
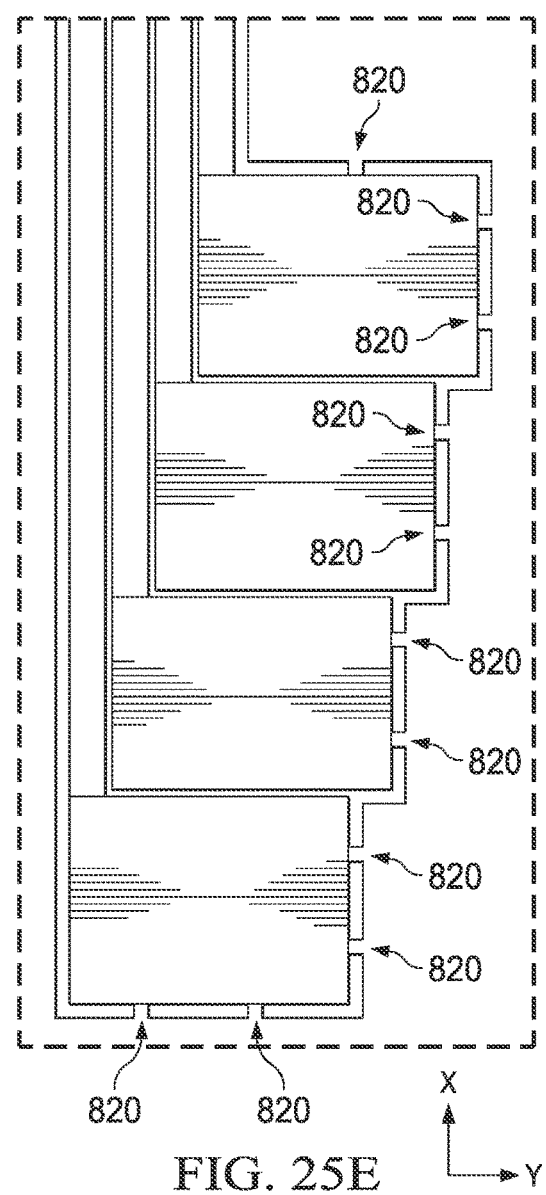
FIG. 25A
FIG. 25E

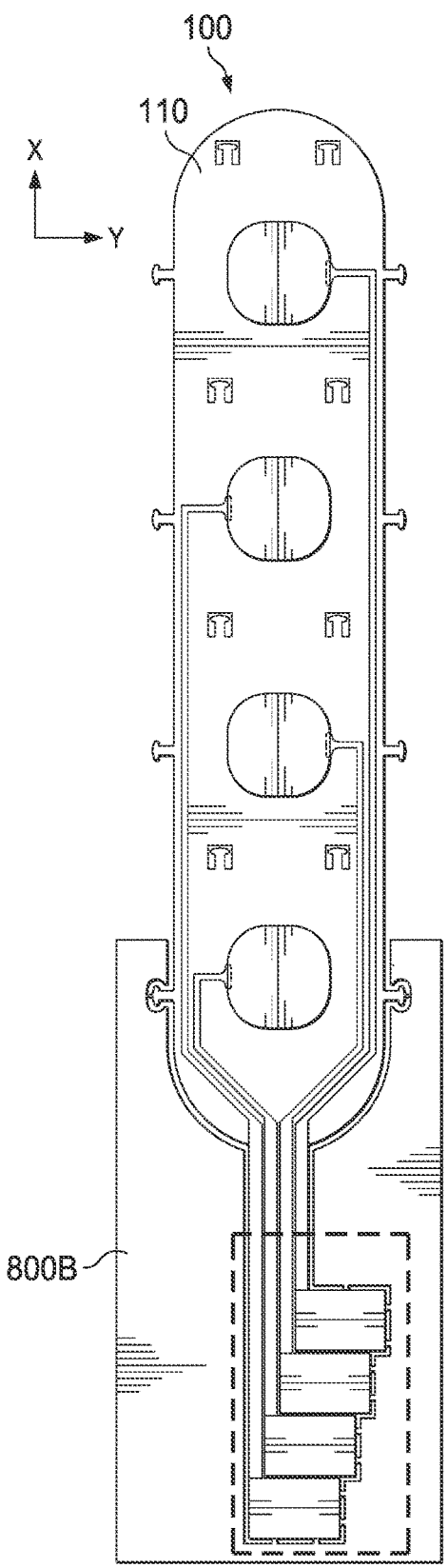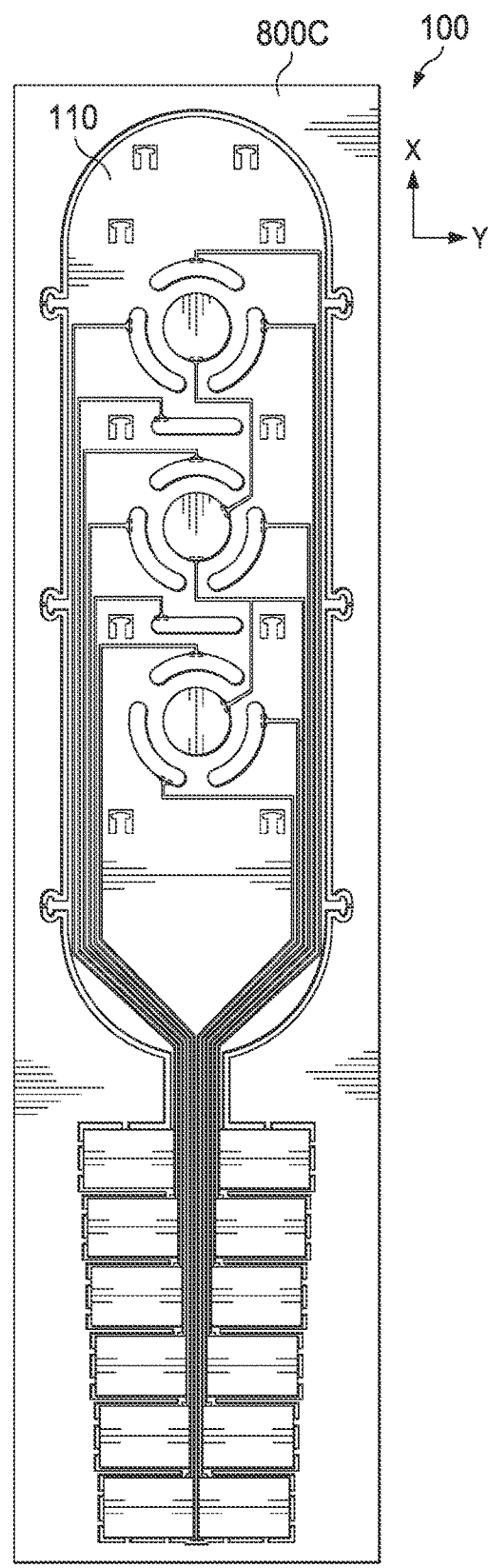
FIG. 25B
FIG. 25C

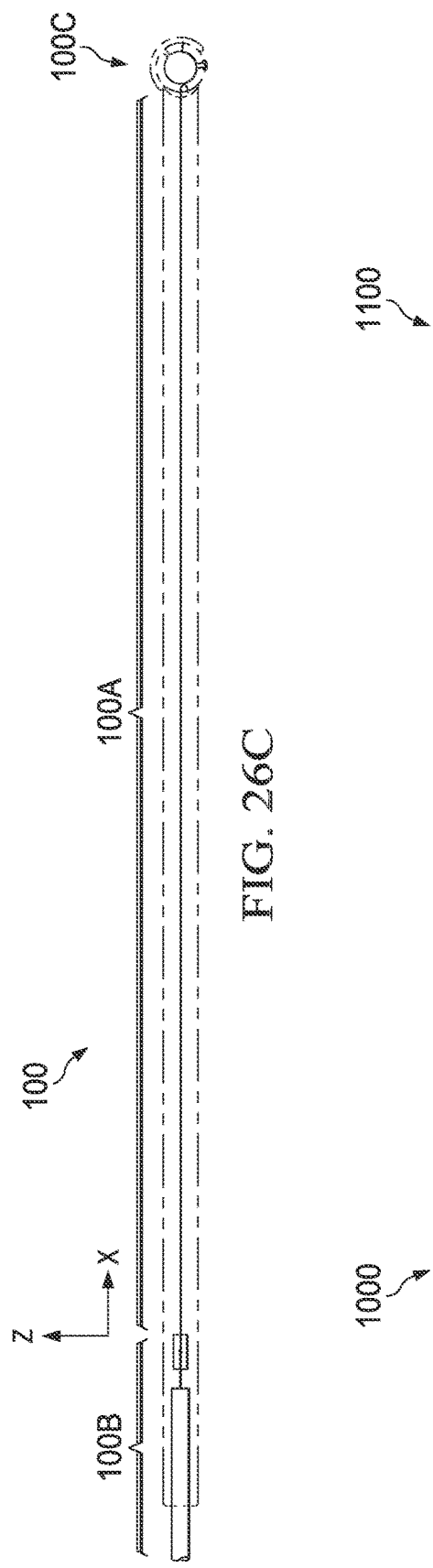
FIG. 26C
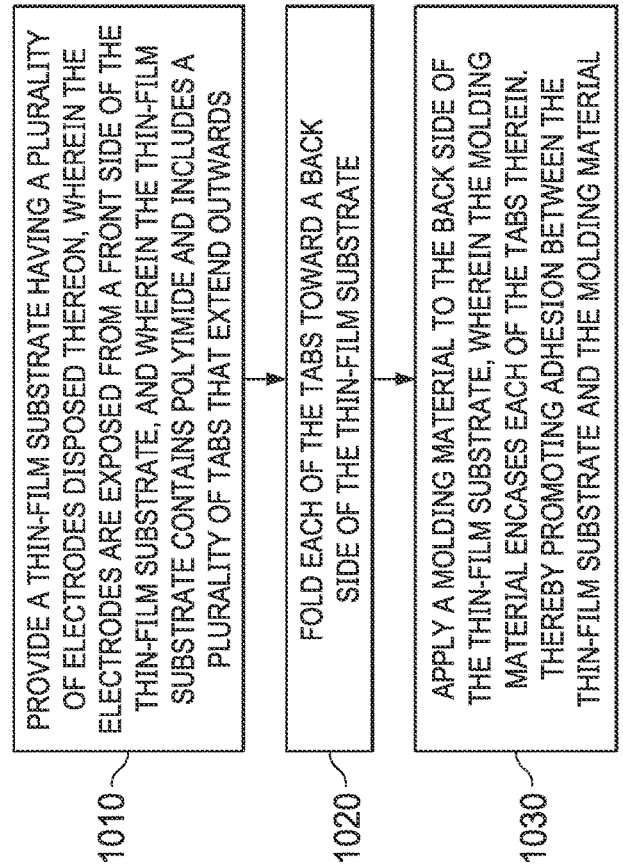
FIG. 28
FIG. 27

CONNECTION MECHANISM FOR THIN FILM STIMULATION LEADS

PRIORITY DATA

The present application is a utility application of U.S. Provisional Application No. 63/002,857, filed on Mar. 31, 2020, entitled "Connection Mechanism for Thin Film Stimulation Leads", the disclosures of each of which are hereby incorporated by reference in their respective entireties.

BACKGROUND

Electrode assemblies are used in several different medical applications to provide electrical stimulation and/or sensing for the treatment of many different conditions. In use, current electrode assemblies are part of a stimulation and/or sensing system, which also includes a cooperating stimulator to produce electrical pulses that can be delivered to an area of the body, or a sensing unit to sense electrical signals. Developing and manufacturing implantable electrode assemblies can be very challenging, since components are often small, fragile and easily damaged. Further, due at least in part to anatomy space constraints, conventional manufacturing methods limit the stimulation contact geometry to effectively stimulate excitable tissue. These situations can lead to higher expense, overly complex products, and electrode assemblies which are not optimum for the desired therapy.

In many applications, it is desirable to produce electrode assemblies which are flexible, but also include the necessary mechanical structures needed to provide the desired electrical stimulation signals. It is also desirable for the electrode assemblies to have sufficient mechanical robustness to survive repeated flex. Unfortunately, manufacturing limitations have historically provided challenges, since certain amounts of backing material has been required to support electrodes. As an example, existing paddle leads used for stimulation in the epidural space are typically 1-3 mm thick so that metal electrodes can be appropriately supported and protected. In several circumstances and applications, however, it is desirable to have an electrode assembly which is thin and pliable, thus avoiding compression of the nerves, while also allowing conformance to the anatomy, comfort, and the ability to provide better stimulation therapy.

Thin films are utilized for several applications in many different products. Manufacturing technologies and materials have evolved so that thin films can be used as a substrate for multiple electrical components. Thin film can be effectively manufactured to include many different signal traces and electrical elements which could potentially provide a structure for the above-referenced electrical stimulation and/or sensing therapy. That said, thin film substrates alone may not have the desired mechanical rigidity to be effectively implanted and/or placed for electrical stimulation therapies. Further, certain types of thin film substrates do not easily bond or adhere to other substances, thus making it difficult or challenging to work with as a desirable substrate.

When contemplating thin film leads, a further complication involves the electrical connection of the electrodes used and the wire/cable supplying electrical stimulation pulses. Again, the size of signal transmission paths on the thin film structures and the materials used create challenges and complications.

In contrast, well-known/common electrode leads are often formed on other substrate materials, which provides strength and rigidity as necessary. That said, the size and structure needed to create a useable substrate can be undesirable in certain situations, since it is not flexible or thin enough. In most cases, these electrodes based upon traditional substrates have a height dimension which can be as high as three millimeters, and thus creates challenges when being implanted.

Therefore, although conventional electrode leads and their method of fabrication have generally been adequate, they have not been entirely satisfactory in all aspects.

BRIEF DESCRIPTION OF THE DRAWINGS

FIG. 3 is a top view of a thin film lead assembly according to an embodiment of the present disclosure.

FIG. 4 is a side view of a thin film lead assembly according to an embodiment of the present disclosure.

FIGS. 8-9 are top views of a thin film lead assembly according to an embodiment of the present disclosure.

FIG. 10 is a side view of a thin film lead assembly according to an embodiment of the present disclosure.

FIGS. 13-14 are side views of a thin film lead assembly according to an embodiment of the present disclosure.

FIGS. 25A-25E are top views of fixtures for thin film lead assemblies according to various embodiments of the present disclosure.

FIGS. 26A-26C are perspective, top, and side views of a thin film lead assembly according to an embodiment of the present disclosure.

FIGS. 27-28 are flowcharts illustrating methods of fabricating a thin film lead assembly according to an embodiment of the present disclosure.

DESCRIPTION

Figure 1:
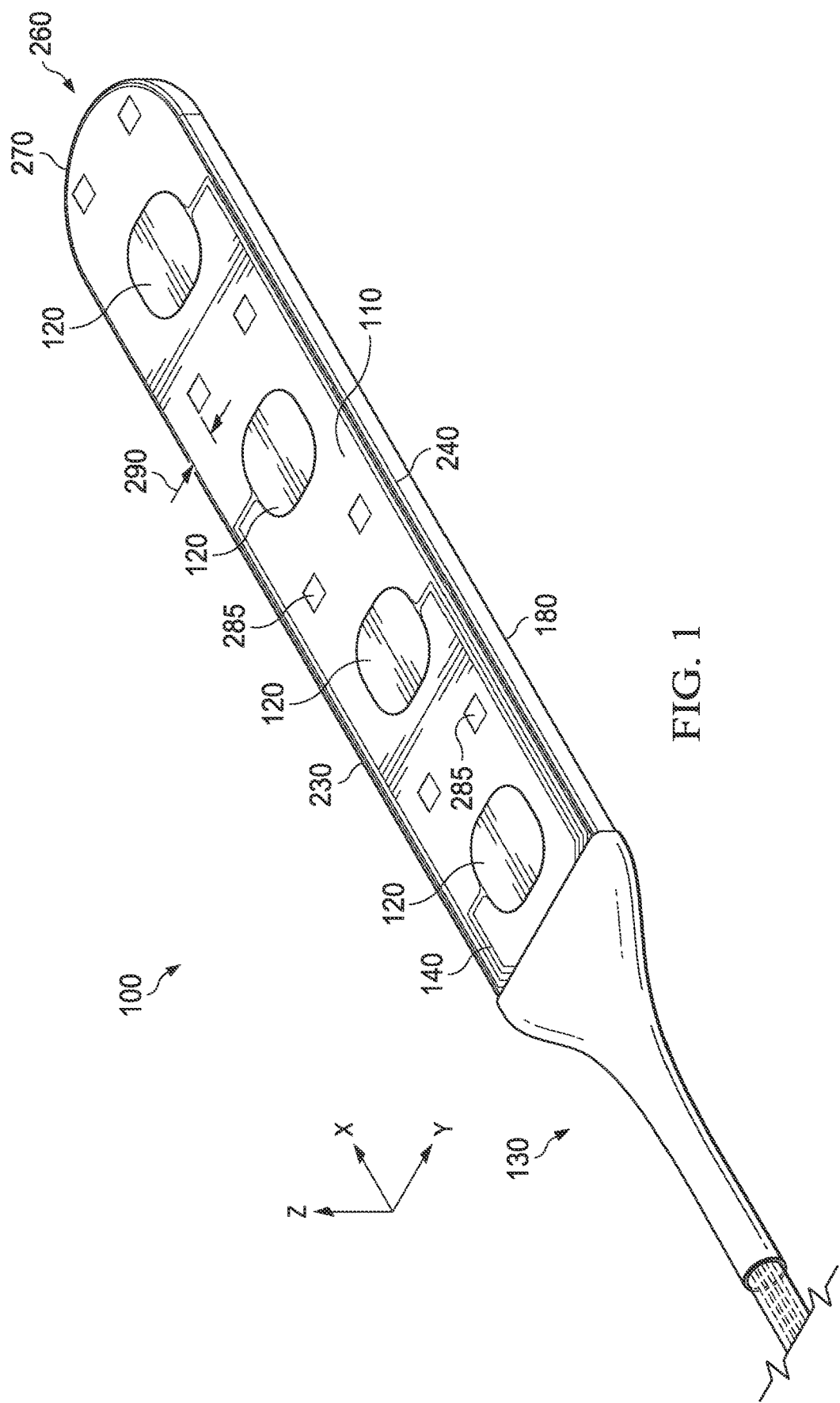
FIGS. 1-2 are three-dimensional perspective views of a thin film lead assembly according to an embodiment of the present disclosure.

Reference will now be made in detail to specific embodiments or features, examples of which are illustrated in the accompanying drawings. Generally, corresponding reference numbers will be used throughout the drawings to refer to the same or corresponding parts. Also, wherever possible, the same reference numbers will be used throughout the drawings to refer to the same or the like parts.

The following disclosure provides many different embodiments, or examples, for implementing different features of the disclosure. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

In addition, the present disclosure may repeat reference numerals and/or letters in the various examples. This repetition is for the purpose of simplicity and clarity and does not in itself dictate a relationship between the various embodiments and/or configurations discussed. Moreover, the formation of a feature on, connected to, and/or coupled to another feature in the present disclosure that follows may include embodiments in which the features are formed in direct contact, and may also include embodiments in which additional features may be formed interposing the features, such that the features may not be in direct contact. In addition, spatially relative terms, for example, "lower," "upper." "horizontal," "vertical," "above," "over," "below." "beneath," "up," "down," "top," "bottom," etc., as well as derivatives thereof (e.g., "horizontally." "downwardly." "upwardly." etc.) are used for case of the present disclosure of one features relationship to another feature. The spatially relative terms are intended to cover different orientations of the device including the features. Still further, when a number or a range of numbers is described with "about," "approximate," and the like, the term is intended to encompass numbers that are within a reasonable range including the number described, such as within +/−10% of the number described or other values as understood by person skilled in the art. For example, the term "about 5 nm" encompasses the dimension range from 4.5 nm to 5.5 nm.

Figure 2:
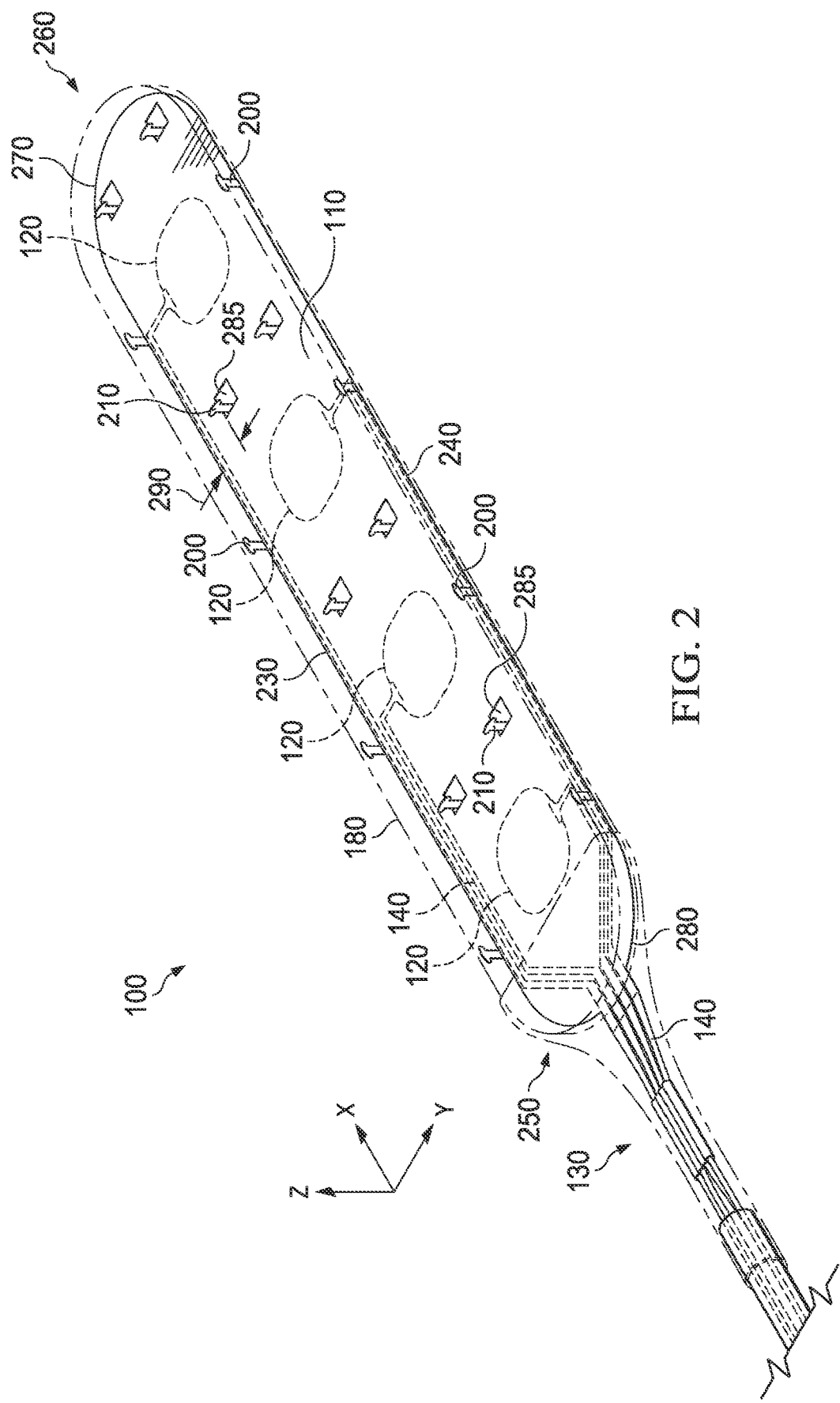

FIGS. 1-4 illustrate various view of a non-limiting embodiment of a lead assembly 100. In more detail, FIG. 1 illustrates a three-dimensional perspective view of a top side (also interchangeably referred to as a front side) of the lead assembly 100. FIG. 2 illustrates a three-dimensional perspective view of a bottom side (also interchangeably referred to as a back side) of the lead assembly 100. FIG. 3 illustrates a planar view of the top side of the lead assembly 100. FIG. 4 illustrates a side view of the lead assembly 100.

The lead assembly 100 includes a thin film substrate 110 (also referred to as a thin film body) supporting a plurality of electrodes 120, and a related wiring assembly 130. In one embodiment, the wiring assembly 130 is configured to be connected to an electrical stimulator (not shown) or electrical pulse generator. Based on programming instructions received from an electronic programmer (e.g., a clinician programmer or a patient programmer), the electrical stimulator or pulse generator can independently deliver electrical stimulation signals to each of the plurality of electrodes 120. To that end, the wiring assembly 130 and the thin film substrate 110 include a plurality of connection traces 140, where each trace 140 is capable of establishing an electrical connection between the electrical stimulator and a corresponding electrode 120. Note that each of the electrodes 120 is positioned on a top side of the thin film substrate 110 and may be flush with the planar surface of the thin film substrate 110, thus allowing for stimulation pulses to be provided to a portion of a patient's body (e.g., spinal cord) when the top side of the lead assembly 100 is appropriately positioned with respect to the patient's body.

Figure 5:
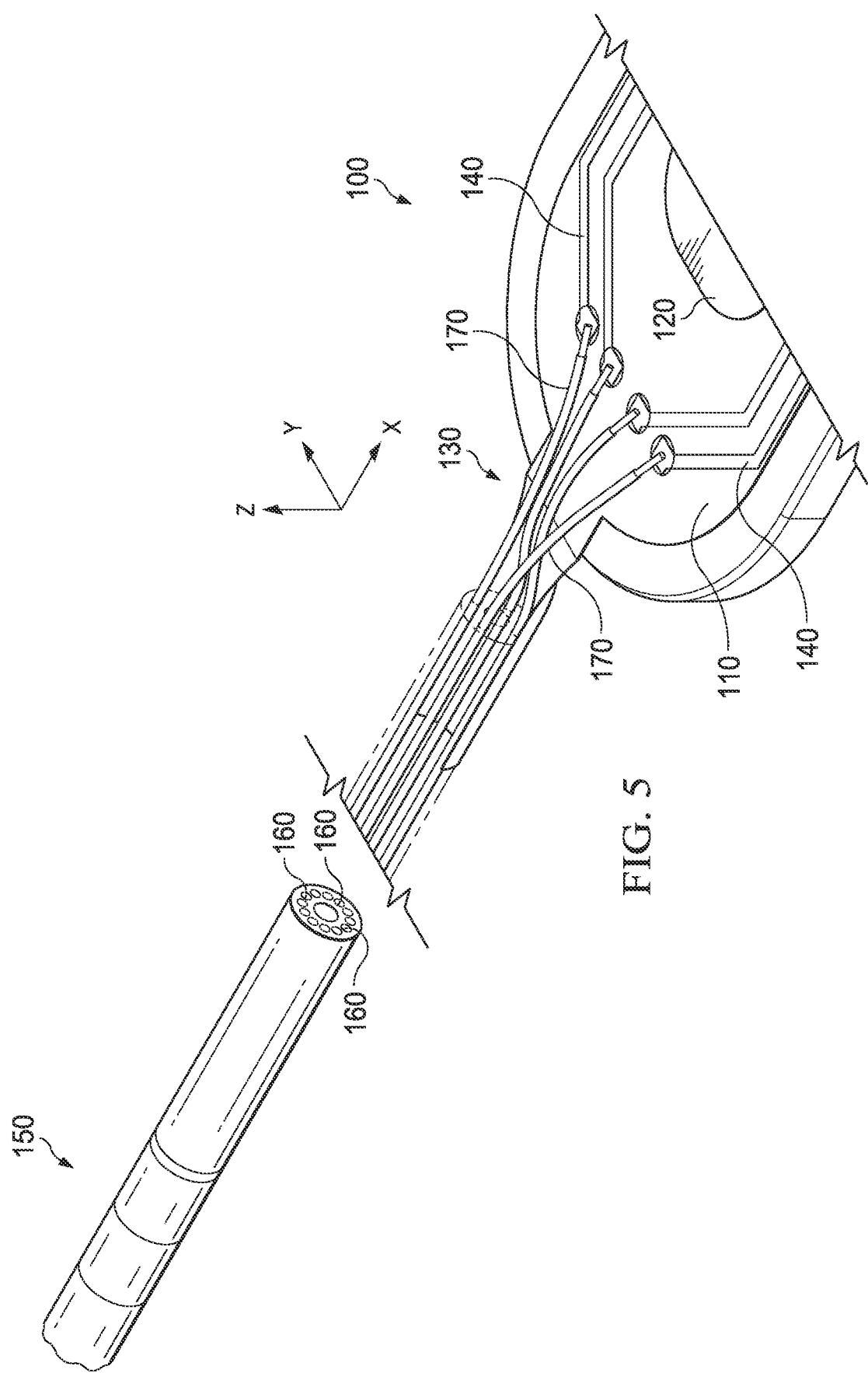
FIG. 5 is a three-dimensional perspective view of multi-lumen lead as an example type of lead and a portion of a thin film lead assembly according to an embodiment of the present disclosure.

For example, FIG. 5 illustrates a multi-lumen lead 150 (as an example type of lead) and a portion of the lead assembly 100. As shown in FIG. 5, the connection traces 140 insure the electrical connection to each of the electrodes 120 when coupled with the multi-lumen lead 150. The multi-lumen lead 150 includes an electrically insulating material containing multiple lumens 160, which are separated and isolated from one another, thereby providing an ability to separately energize multiple electrodes 120 simultaneously. In this embodiment, each of the connection traces 140 is individually connected to a respective one of a plurality of connection wires 170 (also referred to as supply wires). The connection wires 170 are then individually inserted or placed within separate lumens 160, thus achieving the necessary electrical connections between the multi-lumen lead 150 and the connection traces 140. Once the connection traces 140 are appropriately electrically connected to the multi-lumen lead 150 (e.g., via the connection wires 170), the lead assembly 100 can be then encapsulated as desired. As such, the connection traces 140 and connection wires 170 provide an effective and efficient mechanism to achieve electrical connection with the multi-lumen lead 150. It is understood that although the connection traces 140 are illustrated as extending in a single plane herein, these could also be staggered, stacked or designed in alternative arrangements, thereby helping to control the profile of the connection traces and potentially reduce overall size of these structures. It is understood that the multi-lumen lead 150 described herein is merely an example of a lead structure and is not intended to be limiting. In other embodiments, alternative types of lead structures may be used instead.

Referring back to FIGS. 1-4, the thin film substrate 110 is a polyimide thin film substrate, but those skilled in the art will recognize that several alternative materials could also be used. As will also be appreciated by those skilled in the art, polyimide substrates are well understood and generally provide efficient mechanisms to support electrical components. Multilayer structures, such as the polyimide substrate structure, can be easily achieved through existing or known manufacturing processes, thus creating a desired substrate specifically configured to address specific needs. In some embodiments, the thin film substrate 110 may be formed by forming a base polyimide on a glass plate, and forming a target metal layer over the base polyimide. Patternable layers, such as photoresist layers, may be formed over the target metal layer and/over the base polyimide. A plurality of photolithography processes (e.g., including processes such as photoresist exposing, etching, developing, photoresist removal, etc.) are then performed to define the shapes and contours of various components on the polyimide (such as the attachment structures of the present disclosure discussed below in more detail), as well as the connection traces 140 by patterning the target metal layer.

That said, although polyimide substrates offer flexibility due to their extremely thinness (e.g., ranging from several microns to tens of microns, which is thinner than a typical human hair), they are also very fragile, thus creating various challenges in real world fabrication and/or usage. For example, one of the challenges is that polyimide does not easily bond to other materials, such as molding materials. This creates additional manufacturing challenges when trying to incorporate these substrates into other devices. Based upon these challenges, polyimide substrates have not been widely incorporated into various products, including stimulation leads/stimulation electrodes.

The present disclosure overcomes these problems discussed above by implementing anchoring mechanisms as a part of the assembly 100, so that the anchoring mechanisms can provide additional adhesion between the thin film substrate 110 and the molding materials. In more detail, the present disclosure forms stimulation leads at least in part by encasing, over molding, or coating portions of the lead itself (e.g., such as the thin film substrate 110) in a silicone material 180. For example, as a part of an overmolded assembly process, the lead assembly 100 is placed into a mold. Silicone or another type of suitable molding material is then injected into the mold, such that the bottom planar surface of the thin film substrate 110 is attached to the silicone when the silicone is hardened. Advantageously, even though the thin film substrate 110 may lack the mechanical strength or rigidity for implantation in a patient's body, the silicone material may provide the needed mechanical strength or rigidity, thus providing a stable and well-accepted structure that can be used for implantation and electrical stimulation therapy. Alternatively, another thermoplastic or thermoset could be used to encase over mold or coat the lead. In one embodiment, the silicone 180 is used primarily as a topcoat, which is attached to the back side, but not the front side, of the thin film substrate 110. Since the stimulation therapy is delivered by electrodes 120 on the front side of the thin film substrate 110, the application of the silicone on the back side does not adversely affect the operation and effectiveness of the stimulation electrodes 120, even though the silicone provides additional structure to the lead assembly 100.

Unfortunately, as mentioned above, the thin film substrate 110 may not easily adhere to the silicone 180, since it may not be easy for two relatively smooth surfaces (e.g., the planar surfaces of the thin film substrate 110 and the silicone 180) to bond to each other. Even when bonding between the thin film substrate 110 and the silicone 180 is achieved initially, the thin film substrate 110 may peel off from the silicone 180 over time. Such a delamination between the thin film substrate 110 and the silicone 180 may degrade the performance of the lead assembly 100, interfere with the intended operation of the lead assembly, and/or render the lead assembly 100 partially or wholly defective.

To overcome the delamination issue discussed above, the present disclosure implements a plurality of attachment structures, such as attachment structures 200 and attachment structures 210, as specific adhesion structures that are integrated into the thin film substrate 110. In other words, the attachment structures 200 and 210 have the same material composition (e.g., polyimide or another suitable type of material for the thin film substrate) as the thin film substrate 110 itself, and they are fabricated alongside the thin film substrate 110 using the same fabrication processes, for example via the same lithography processes that were used to define the shapes and contours of the thin film substrate 110. Or stated differently, the attachment structures 200 and 210 may be viewed as an integral part of the thin film substrate 110 itself, but their unique shapes and locations allow them to be bent in a direction away from the rest of the thin film substrate 110 and into or toward the silicone 180, so as to increase the adhesion between the thin film substrate 110 and the silicone 180, as will be discussed in more detail below.

In the embodiment illustrated in FIGS. 1-4, eight attachment structures 200 and eight attachment structures 210 are implemented at predetermined locations on the thin film substrate 110, though only some of them are specifically labeled herein for reasons of simplicity. The attachment structures 200 may be referred to as "edge tabs", since they are each located on an edge 230 or on an edge 240 of the thin film substrate 110. In that regard, the thin film substrate 110 extends in an elongated manner in an X-direction from a first end 250 to a second end 260, where the electrodes 120 are separated from one another in the X-direction. The planar view of FIG. 3 is defined by the X-direction and a Y-direction that is perpendicular to the X-direction, the side view of FIG. 4 is defined by the X-direction and a Z-direction that is orthogonal to the plane defined by the X-direction and the Y-direction. The three-dimensional perspective views of FIGS. 1-2 illustrate all three of the directions in the X, Y, and Z axis.

As shown in FIGS. 1-3, the planar surface of the thin film substrate 110 has straight edges 230 and 240, which each extend in the X-direction and are spaced apart from one another in the Y-direction. The straight edges 230 and 240 are joined together by rounded edges 270 and 280, which partially extend in both the X-direction and the Y-direction. In the illustrated embodiment, the attachment structure 200 are implemented on the straight edges 230 and 240, but it is understood that they may also be implemented on the rounded edges 270 and 280 in other embodiments.

In comparison to the attachment structures 200, the attachment structures 210 (shown in FIG. 2) are each located in an internal region of the planar surface of the thin film substrate 110, away from the edges 230/240/270/280. Furthermore, the attachment structures 210 have been "lifted" down from the planar surface of the thin film substrate 110 toward the back side (as will be discussed in more detail below), which will leave a window 285 or a cutout 285 in the planar surface for each respective attachment structure 210. As such, the attachment structures 210 may also be referred to as "internal tabs" or "internal cutout tabs." For example, each of the attachment structures 210 may be spaced apart from the nearest edge (e.g., the straight edge 230) by a respective distance 290. In the illustrated embodiment, the distance 290 is measured in the Y-direction. Since the distance 290 directly determines the location of each attachment structure 210 on the thin film substrate 110, the value of the 290 may be configured such that the attachment structures 210 are distributed relatively uniformly throughout the planar surface of the thin film substrate 110. The relatively uniform distribution of the locations of the attachment structures 210 leads to a relatively uniform distribution of the adhesion forces between the attachment structures 210 and the silicone 180.

Figure 6A:
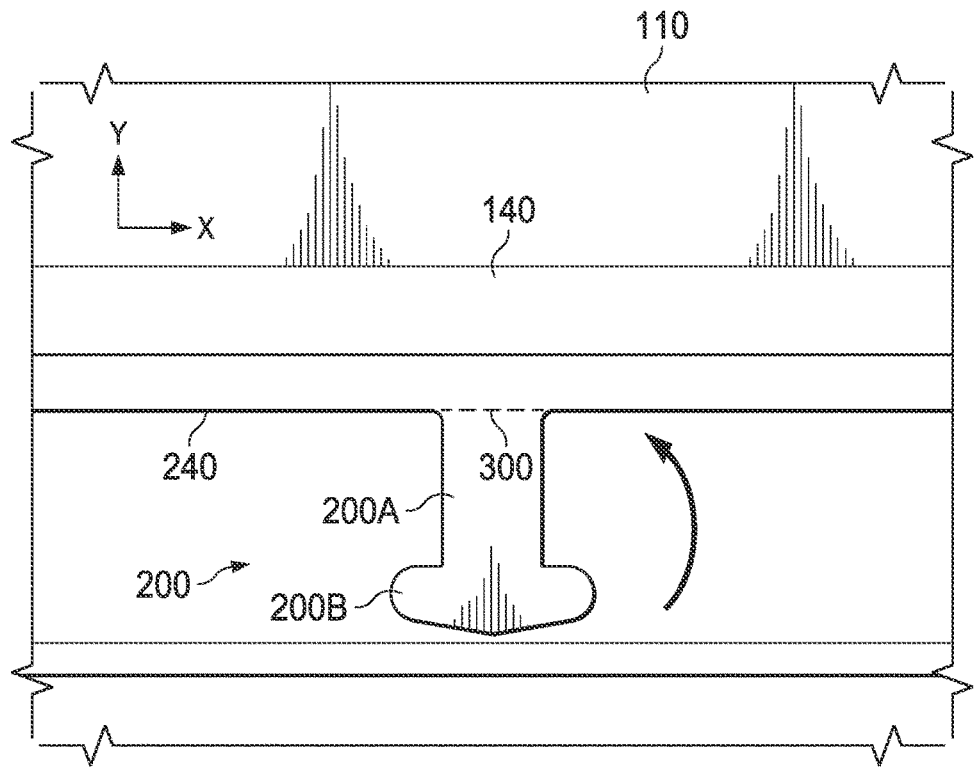
FIGS. 6A-6B each illustrate a magnified top view of attachment structures of a thin film lead assembly according to an embodiment of the present disclosure.
Figure 6B:
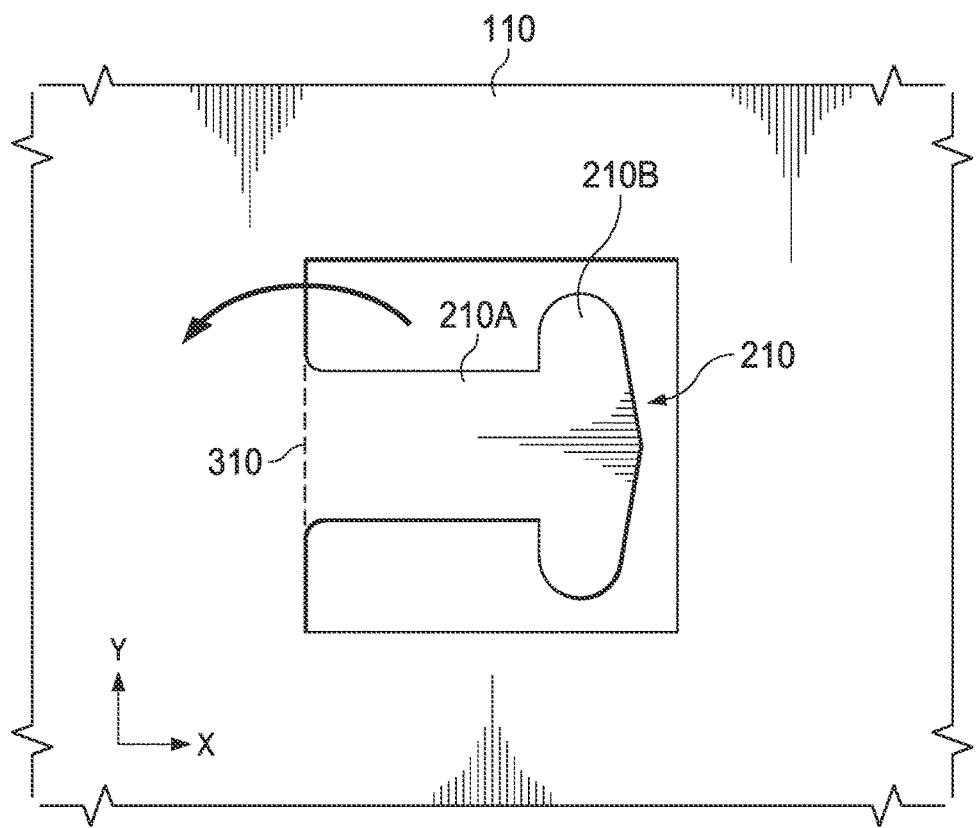

To facilitate the discussion of the attachment structures 200 and 210, FIGS. 6A and 6B illustrate magnified planar views of the attachment structure 200 and the attachment structure 210 (also referred to as adhesion structures), respectively. With reference to FIGS. 1-4 and 6A-6B, the attachment structures 200 and 210 each have a "T-bar" like shape. In other words, the planar view profile or contour of the attachment structures 200 and 210 resemble the capitalized letter "T". For example, the attachment structure 200 includes a body portion 200A and a head portion 200B. The body portion 200A is connected to the edge 240 (or edge 230) of the thin film substrate 110 and extends away from the edge 240 in the Y-direction. The head portion 200B is connected to the body portion 200A and extends in the X-direction. In other words, a dimension of the head portion 200B in the X-direction is substantially greater than a dimension of the head portion 200B in the Y-direction, and the dimension of the head portion 200B in the X-direction is also substantially greater than a dimension of the body portion 200A in the X-direction. Since the attachment structures 200 are located at the edges 230 and 240 of the thin film substrate 110, they may also be referred to as "edge tabs."

Similarly, the attachment structure 210 includes a body portion 210A and a head portion 210B. The body portion 210A is connected to the planar surface of the thin film substrate 110 (or may be reviewed as a part of the planar surface if the thin film substrate 110) and extends in the X-direction. The head portion 210B is connected to the body portion 210A and extends in the Y-direction. In other words, a dimension of the head portion 210B in the Y-direction is substantially greater than a dimension of the head portion 210B in the X-direction, and the dimension of the head portion 210B in the Y-direction is also substantially greater than a dimension of the body portion 210A in the Y-direction.

The attachment structures 200 and 210 are foldable or bendable prior to being encased in the silicone 180, so that they can protrude at an angle away from the planar surface of the thin film substrate 110 before being encased in the silicone 180. For example, the attachment structure 200 is foldable or bendable in the Y-direction and the Z-direction with respect to an imaginary axis 300 (illustrated in FIG. 6A as dashed lines). That is, the attachment structure 200 can be folded or bent along the imaginary axis 300, such that it protrudes away from the planar surface of the thin film substrate 110 at an angle, where the angle is defined by the Z-direction and the planar surface of the thin film substrate 110. In some embodiments, the angle may be substantially 90 degrees. In other words, the attachment structure 200, after being bent or folded, is "coming straight out of the paper" in FIG. 6A. Similarly, the attachment structure 210 may be folded or bent in the X-direction and the Z-direction along an imaginary axis 310, such that it is "coming straight out of the paper" in FIG. 6B.

The attachment structures 200 and 210 promote adhesion with the silicone 180. In more detail, in some embodiments before the thin film substrate 110 is placed into a mold as part of the overmolded assembly process, the attachment structures 200 and 210 are folded or bent to protrude away from the planar surface of the thin film substrate 110 toward the bottom side (e.g., 90 degrees away from the planar surface and toward the bottom side). Thereafter, the lead assembly 100 (with the bent/folded attachment structures) is placed into a mold, and silicone 180 is injected into the mold. When silicone 180 is hardened, the protruded attachment structures 200 and 210 will be encased in (or surrounded by) the silicone 180 from the bottom side of the thin film substrate 110. In this manner, the adhesion between the silicone 180 and the thin film substrate 110 comes not just from a two-dimensional contact area between the planar back surface of the thin film substrate 110 and the silicone 180, but also from the enclosure of the raised (e.g., in the Z-direction) attachment structures 200 and 210 within the silicone 180. Stated alternatively, the bending of the attachment structures 200 and 210 provides a three-dimensional physical connection between the thin film substrate 110 and the encasing material such as the silicone 180. Each attachment structure 200 and 210 provides a separate connection point for the silicone 180 (or another suitable type of outer molding material), thus allowing for enhanced adhesion between the silicone 180 and the thin film substrate 110 and reducing the likelihood of delamination. It is understood, however, that the folding or bending of the attachment structures 200 and 210 is optional (and not required) to achieve better adhesion between the thin film substrate 110 and the silicone 180. In other words, even without being folded or bent, the mere presence of the attachment structures 200 and 210 alone may be capable of promoting adhesion between the thin film substrate 110 and the silicone 180.

The fact that the head portions 200B and 210B are wider (in the X-direction and Y-direction, respectively) than their respective body portions 200A and 210A may further prevent delamination of the silicone 180 from the thin film substrate 110, since such a delamination would pull the attachment structures 200 and 210 away from the thin film substrate 110, but the wider head portions 200B and 210B would resist such a pulling force (i.e., the delamination force) more effectively, thereby making the adhesion between the thin film substrate 110 and the silicone 180 stronger and their delamination even less likely to occur.

In addition, the fact that the attachment structures 200 and 210 are oriented in different directions (e.g., the head portion 200B of the attachment structure 200 extending in the X-direction VS the head portion 210B of the attachment structure 210 extending in the Y-direction) means that the attachment structures 200 and 210 resist being pulled in both the X-direction and the Y-direction, which further increases the amount of force required to delaminate the thin film substrate 110 from the silicone 180. Consequently, the design of orienting the attachment structures 200 and 210 in different (e.g., perpendicular) directions enhances the adhesion between the thin film substrate 110 and the silicone 180.

Furthermore, in embodiments when the attachment structures 210 (i.e., the internal "cutout tabs") are implemented, the silicone (or thermoplastic or thermoset) will fill the "cutout" areas or windows 285 that are formed as a result of the attachment structures 210 being lifted. The presence of the silicone 180 filling these cutout areas or windows 285 creates additional holding structures, which again helps to capture the thin film substrate 110 or promote its adhesion with the silicone 180.

Based on the above discussions, it can be seen that by utilizing specifically designed physical structures such as the attachment structures 200 and/or attachment structures 210, the present disclosure can implement a thin film substrate 110 (e.g., a polyimide substrate) to achieve the desired flexibility and thinness associated with the thin film materials, and at the same time, not suffer from the delamination problems that have plagued traditional thin film leads. As such, the lead assembly 100 of the present disclosure can efficiently and effectively deliver stimulation therapy.

It is understood that although the attachment structures 200 and 210 are implemented with a T-shaped profile in the illustrated embodiment, such a profile is not intended to be limiting. Other configurations and/or geometries could also be used to implement the attachment structures 200 and/or 210. For example, the attachment structures 200 and 210 may not necessarily include a head portion that is differently shaped than the body portion, or they may have differently shaped head portions (e.g., wider, narrower, or exhibit different degrees of curvature), or they may even have multiple head portions, depending on design requirements and manufacturing capabilities and considerations.

Figure 7:
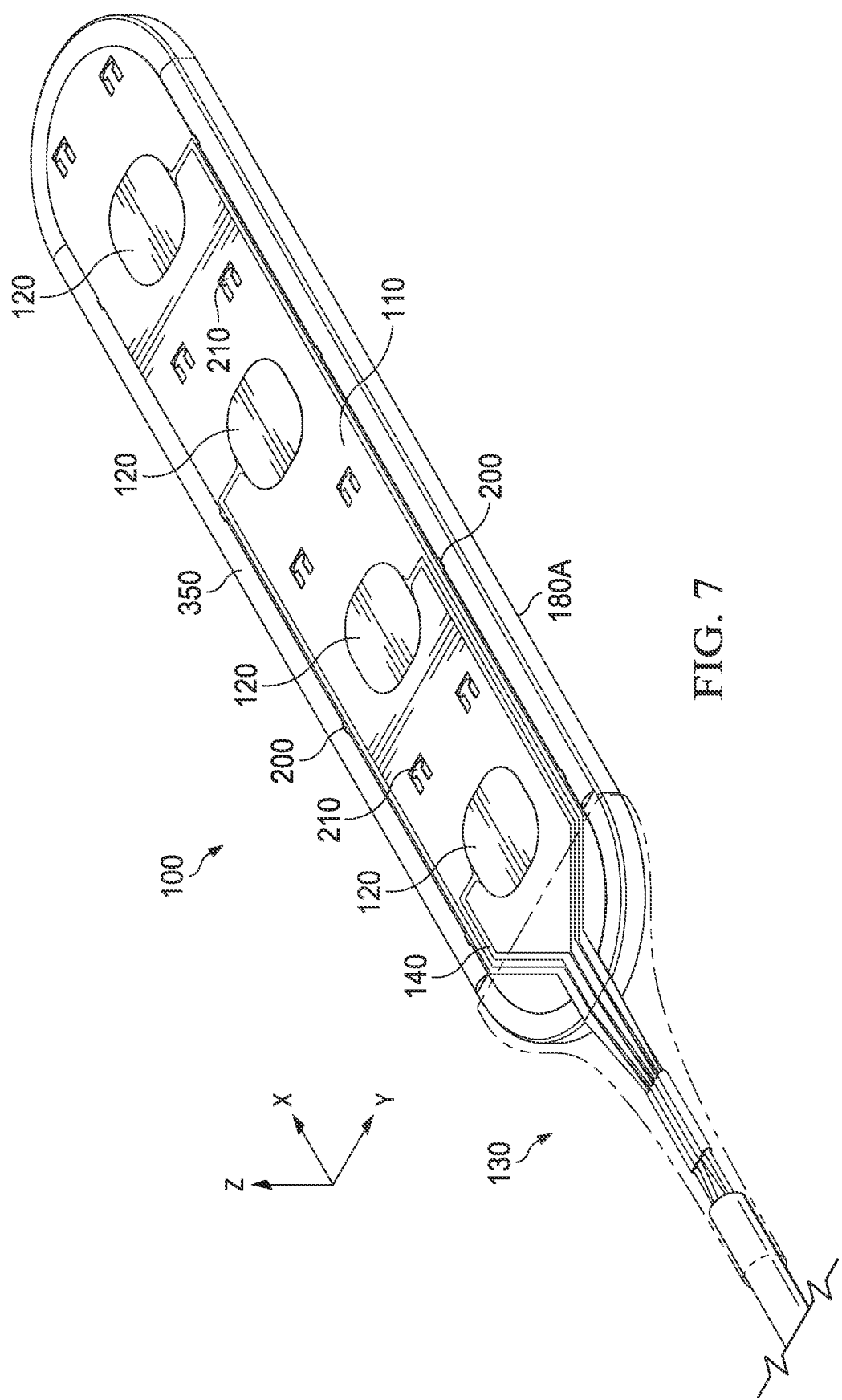
FIG. 7 is a three-dimensional perspective view of a thin film lead assembly according to an embodiment of the present disclosure.
Figure 8:
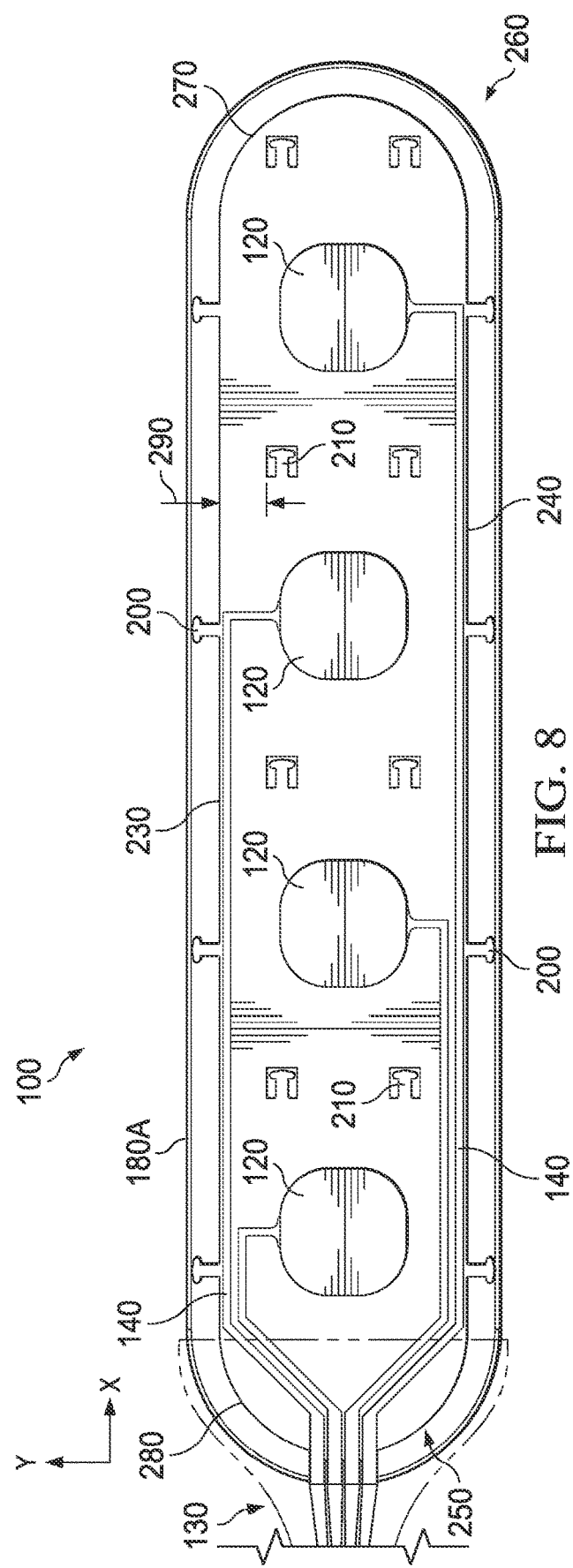

The embodiment discussed above pertains to a paddle lead implementation of the lead assembly 100, where the attachment structures are bent and protrude into the silicone 180 to promote adhesion. FIGS. 7-10 illustrate another embodiment of the lead assembly 100 (still as a paddle lead), where the attachment structures are not bent but rather are coplanar or flush with the rest of the thin film substrate. In more detail, FIG. 7 illustrates a three-dimensional perspective view of a top/front side of the lead assembly 100. FIG. 8 illustrates a planar view of the top/front side of the lead assembly 100 without showing a silicone adhesive. FIG. 9 illustrates a planar view of the top/front side of the lead assembly 100 with the silicone adhesive shown. FIG. 10 illustrates a side view of the lead assembly 100. For reasons of consistency and clarity, similar components appearing in FIGS. 1-10 will be labeled the same.

As shown in FIGS. 7-10, the lead assembly 100 in this embodiment also includes the thin film substrate 110, the electrodes 120, the wiring assembly 130, the conductive traces 140, as well as the attachment structures 200 and 210. However, unlike the embodiment shown in FIGS. 1-4, where the attachment structures 200 and 210 are folded to protrude into the silicone 180 at the bottom side, the attachment structures 200 and 210 are not folded but are rather flush or coplanar with the rest of the thin film substrate 110. For example, as shown clearly in FIG. 8, the attachment structures 200 extend laterally outward from the thin film substrate 110 in the Y-direction. Rather than placing the lead assembly into a mold with the attachment structures 200/210 bent toward the bottom side, the lead assembly 100 in this embodiment is attached to a pre-molded silicone paddle backing 180A. Therefore, the bottom surfaces of the attachment structures 200 and 210 also come into direct physical contact with the pre-molded silicone paddle backing 180A.

To further increase adhesion between the thin film substrate 110 and the pre-molded silicone paddle backing 180A, a thin layer of silicone adhesive 350 is applied over the top surface of the attachment structures 200 after the bottom planar surface of the thin film substrate 110 is attached to the pre-molded silicone paddle backing 180A. As such, both the top surface and the bottom surface of the attachment structures 200 are surrounded by silicone. In other words, the attachment structures 200 protrude laterally (in the Y-direction) into a silicone structure formed by the pre-molded silicone paddle backing 180A and the thin layer of silicone adhesive 350. The majority of the top planar surface of the thin film substrate 110 is still free of having silicone disposed thereon, though some small amounts of the thin layer of silicone adhesive 350 may leak onto the edge regions of the top planar surface of the thin film substrate 110 in some devices. Regardless, the encasement of the laterally-protruding attachment structures 200 in the silicone material still offers sufficient adhesion between the thin film substrate 110 and the pre-molded silicone paddle backing 180A, such that delamination concerns are substantially alleviated.

Note that the attachment structures 210 need not be bent to be encased in the pre-molded silicone paddle backing 180 in this embodiment, which may simplify fabrication of the lead assembly 100. It is also understood that the thin layer of silicone adhesive 350 may or may not have the same material composition as the pre-molded silicone paddle backing 180A. For example, in some embodiments, the pre-molded silicone paddle backing 180A may be configured to have more rigidity than the thin layer of silicone adhesive 350, but the thin layer of silicone adhesive 350 may be configured to be have greater adhesive properties than the pre-molded silicone paddle backing 180A. This is because the pre-molded silicone paddle backing 180A needs to provide form and structure to the lead assembly, whereas the thin layer of silicone adhesive 350 needs to firmly attach itself to the attachment structures 200 (and by extension, the thin film substrate 110) and to the pre-molded silicone paddle backing 180A.

Figure 11:
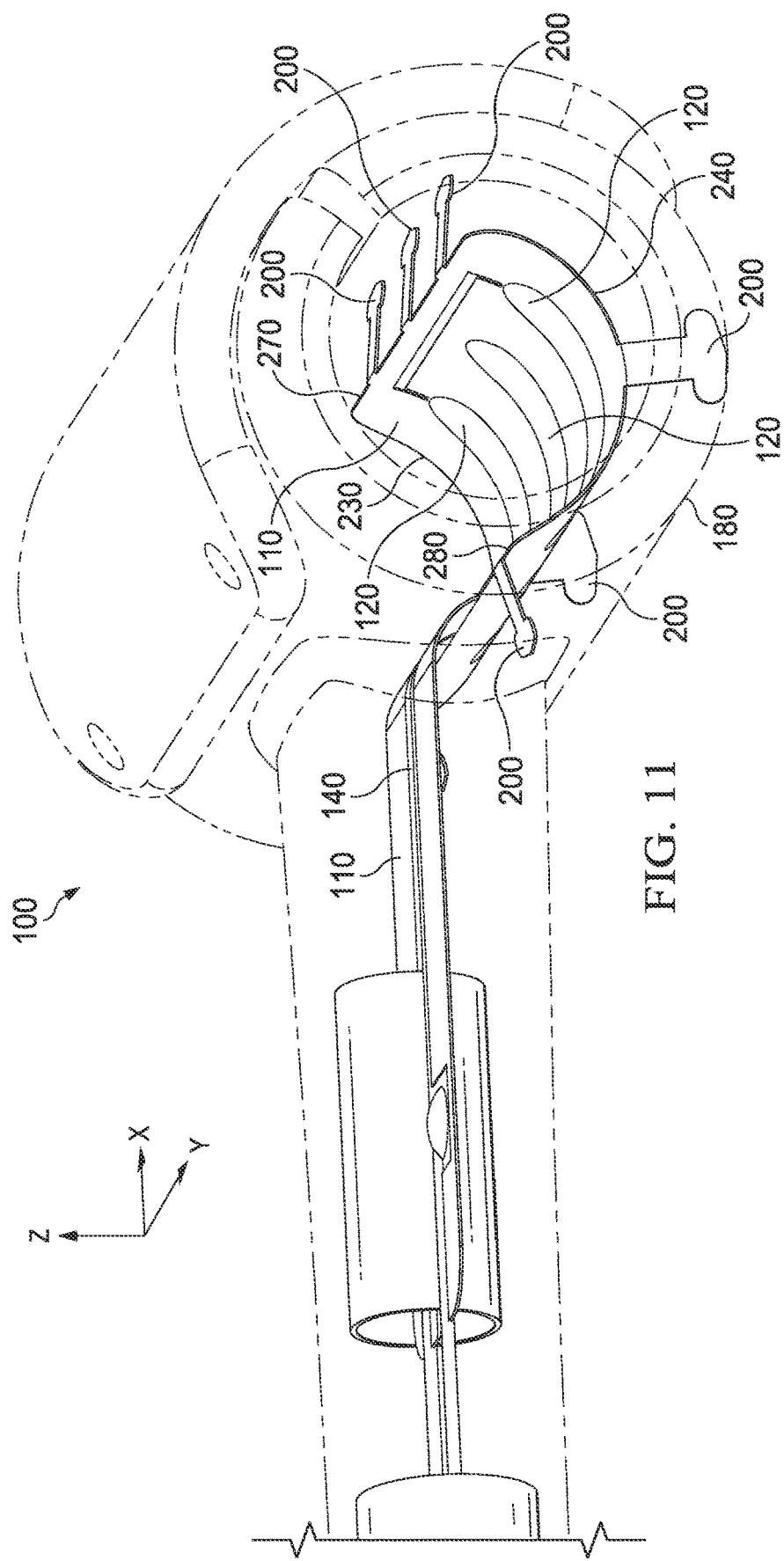
FIGS. 11-12 are three-dimensional perspective views of a thin film lead assembly according to an embodiment of the present disclosure.
Figure 12:
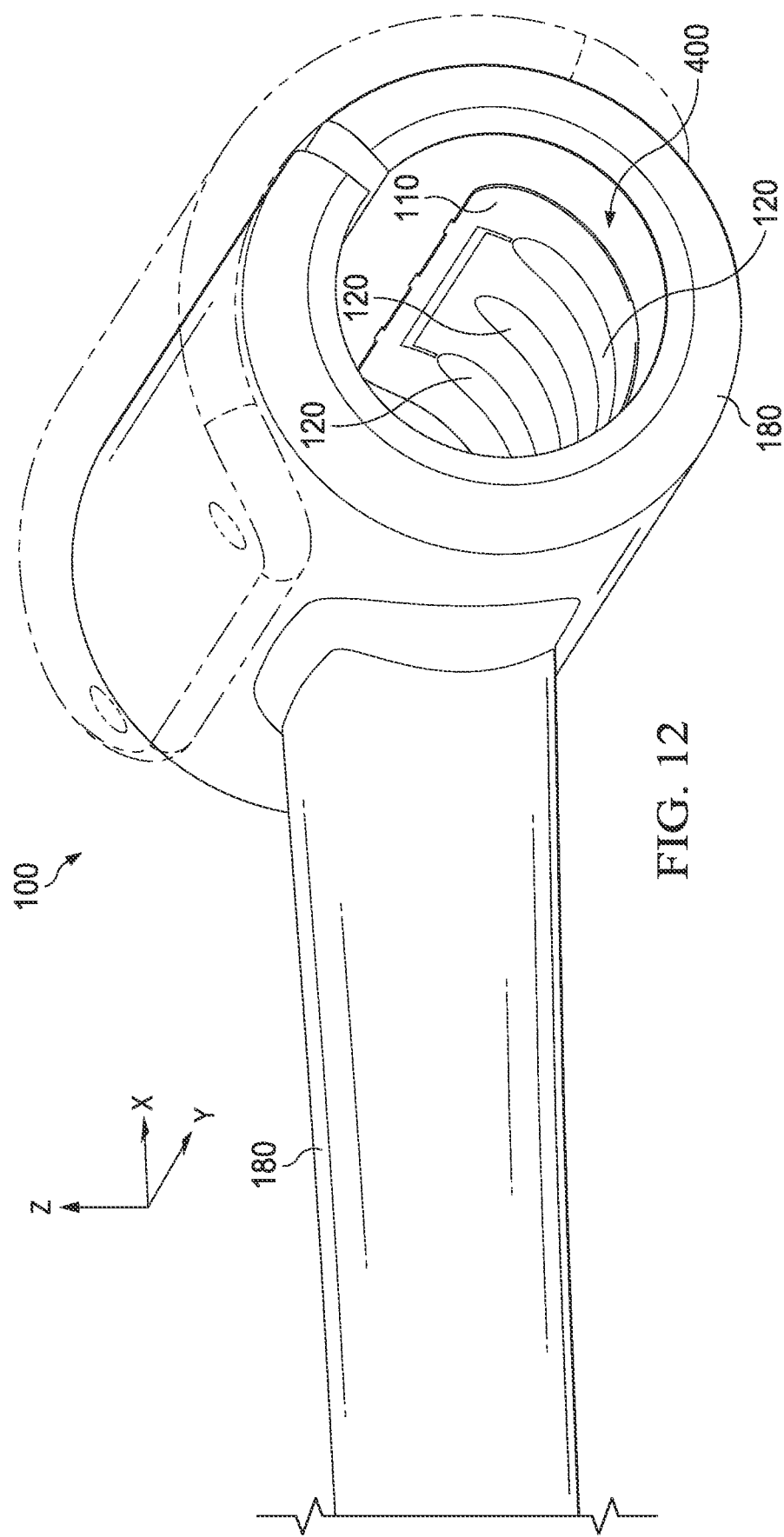
Figure 15:
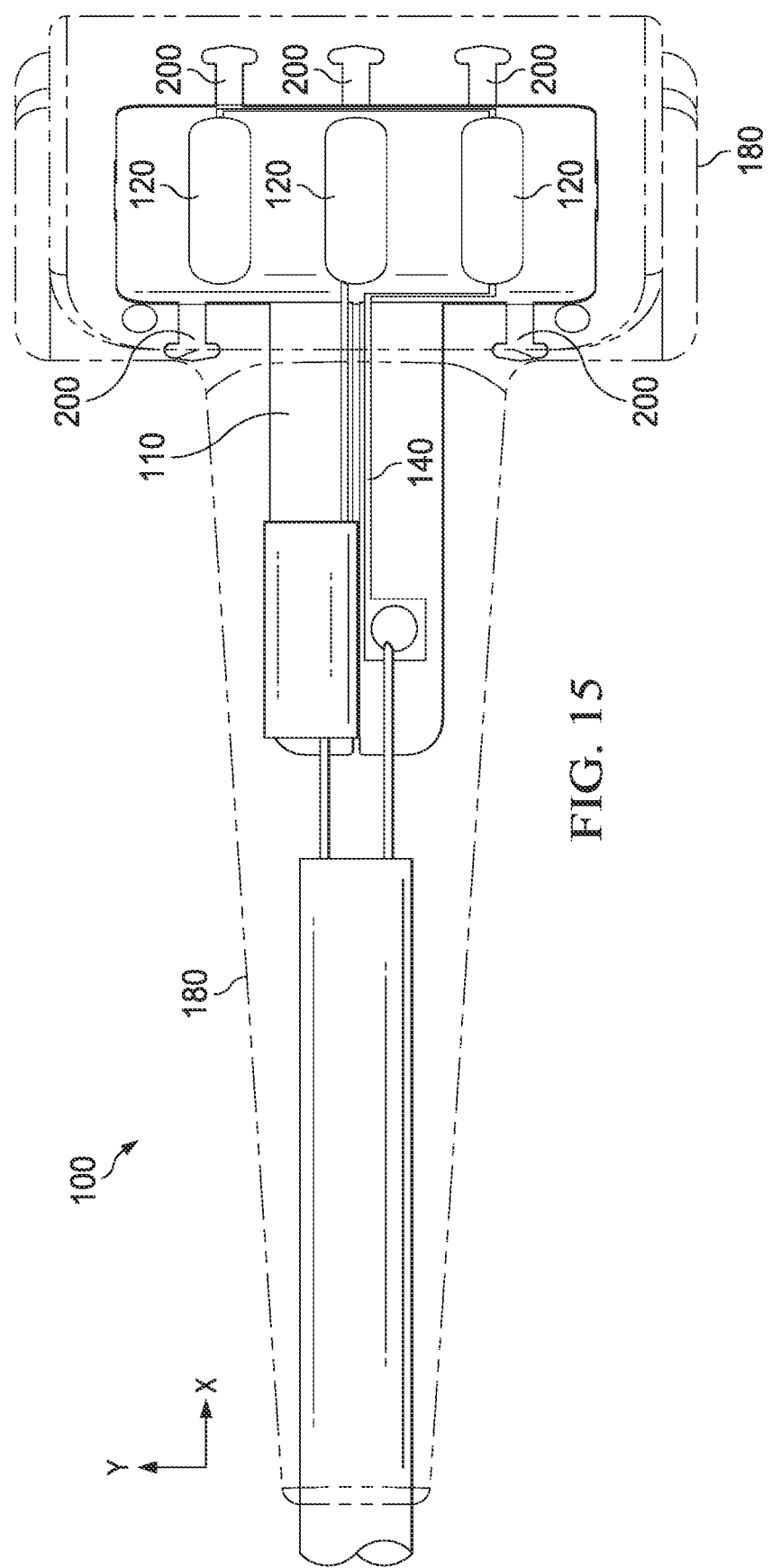
FIG. 15 is a top view of a thin film lead assembly according to an embodiment of the present disclosure.

The two embodiments discussed above each pertains to a paddle lead implementation of the lead assembly 100, one with bent attachment structures, and the other one with unbent attachment structures. FIGS. 11-15 illustrate another embodiment of the lead assembly 100, which is a cuff lead. Specifically, FIG. 11 illustrates a three-dimensional perspective view of the lead assembly 100, where the silicone 180 is illustrated transparently, and where the three dimensions are defined by the X, Y, and Z directions discussed above. FIG. 12 illustrates a three-dimensional perspective view of the lead assembly 100, where the silicone 180 is illustrated non-transparently, and where the three dimensions are also defined by the X, Y, and Z directions discussed above. FIG. 13 illustrates a side view of the lead assembly 100, where the silicone 180 is illustrated transparently. FIG. 14 illustrates a side view of the lead assembly 100, where the silicone 180 is illustrated non-transparently. FIG. 15 illustrates a top view of the lead assembly 100, where the silicone 180 is illustrated transparently. The lead assembly 100 shown in FIGS. 1-4 and 7-10 may hereinafter be interchangeably referred to as a paddle lead assembly, whereas the lead assembly 100 shown in FIGS. 11-15 may be interchangeably referred to as a cuff lead assembly. For reasons of consistency and clarity, similar components appearing in both the paddle lead embodiments and the cuff lead embodiment will be labeled the same.

With reference to FIGS. 11-15, the cuff lead assembly 100 also includes the thin film substrate 110 on which the electrodes 120 are located to deliver electrical stimulation and/or provide electrical sensing. Unlike the paddle lead assembly 100 (whose thin film substrate 110 has flat planar front and back side surfaces), the thin film substrate 110 of the cuff lead assembly 100 has a curved planar front and back side surfaces. For example, as shown in FIGS. 12-14, the silicone 180 is shaped cylindrically and defines an opening 400. The front side of the planar surface of the thin film substrate 110 is exposed to the opening 400, whereas the back side of the planar surface is covered by the silicone 180. Whereas the flatness of the paddle lead assembly 100 makes it suitable for spinal cord stimulation, the curvature of the cuff lead assembly 100 allows it to be used in peripheral nerve stimulation. For example, a peripheral nerve may run through the opening 400, such that the front side of the electrodes 120 (see FIG. 12) may stimulate the peripheral nerve that is runs through the opening 400.

Similar to the paddle lead assembly discussed above, the electrodes 120 in the cuff lead assembly 100 also have co-planar surfaces with the thin film substrate 110. Stated differently, the exposed surfaces of the electrodes 120 are flush with the planar surface of the thin film substrate at the front side. The back side of the electrodes are also covered up by the silicone 180. As is the case for the paddle lead, the silicone 180 in the cuff lead assembly 100 also does not directly extend to the front side but is located only to the back side of the thin film substrate 110. In other words, no silicone 180 comes into direct physical contact with the front side of the planar surface of the thin film substrate 110. As discussed above, the absence of the silicone 180 at the front side planar surface of the thin film substrate 110 is beneficial, since it reduces the likelihood of the electrodes 120 being pushed away from the target nerve by the "lip" created by what would be the silicone on the front side of the thin film substrate 110. Here, since the front side of the thin film substrate 110 has no silicone 180 (or other types of encasement or molding material) disposed directly thereon, the electrodes 120 can be positioned very close to the target nerves.

The attachment structures 200 of the cuff lead assembly 100 also helps the thin film substrate 110 adhere to the silicone 180, for reasons similar to those discussed above with respect to the paddle lead assembly. In the embodiment shown herein, the attachment structures 200 of the cuff lead assembly 100 also have T-shaped profiles, for example having a wider head portion and a narrower body portion. The attachment structures 200 extend away from the thin film substrate 110 toward the back side, for example at a 90-degree angle with respect to the edge that connects the attachment structure 200 to the thin film substrate 110.

One difference between the paddle lead assembly and the cuff lead assembly is that the cuff lead assembly 100 has one or more attachment structures not only on the edges 230 and 240, but also on the edges 270 and 280 of the thin film substrate 110. The exact number of the attachment structures located on each edge is not intended to be limiting, and other embodiments may implement a different number of attachment structures on each of the edges 230, 240, 270, and 280, and the attachment structures 200 may be located at different locations along the edges 230, 240, 270, and/or 280 than what is shown in the illustrated embodiment herein. Regardless of the number or location of the attachment structures 200, their implementation as an integral component of the cuff lead assembly 100 results in improved adhesion between the thin film substrate 110 and the silicone 180, since the attachment structures 200 reach into, and are surrounded by, the silicone 180 three-dimensionally. As a result, delamination problems plaguing conventional thin film leads are less likely to occur herein.

It is also understood that although the illustrated embodiment of the cuff lead assembly does not have the attachment structures 210 (i.e., the internal "cutout tabs"), that is also not intended to be limiting. In other embodiments of the cuff lead assembly 100, the attachment structures 210 may also be implemented on the thin film substrate 110 at an internal region on the back side, so that these attachment structures 210 will help create further adhesion between the thin film substrate 110 and the silicone 180 by extending into and grabbing onto the silicone 180 located at the back side of the thin film substrate 110.

As generally suggested above, the disclosed design and manufacturing methodology allows for thin film substrates to be utilized as a basis for stimulation leads. The resulting encapsulated assembly is relatively thin and flexible, thus providing a more efficient and effective lead structure. This will generally result in better tissue responses, patient comfort and efficiencies. Example applications for the lead assembly generally discussed above include cortical stimulation and maxillofacial implants. Other options and applications could easily be contemplated, especially given the flexibility and thin profile of the lead assembly.

While the above-mentioned flexibility for the lead assembly 100 provides many advantages, circumstances exist where this same flexibility could provide challenges for implantation or placement. To address this potential complication, one alternative is to add a stylet lumen to the finished/encased electrode assembly which will be configured to provide a desired level of rigidity. Many variations are possible, but one design would provide a stylet lumen that would extend to a distal end of the electrode assembly, thereby providing several desirable features which will aid in the placement and implantation. As a further alternative, stiffening members could be included as part of the assembly. Naturally, such stiffening members could extend partially around the substrate, or could extend in specified locations/positions. Again, several alternatives and configurations for stiffening members could be contemplated and developed. By using stiffening members and/or stylet lumens, the physical characteristics (i.e., flexibility, configuration, pliability, etc.) can be easily modified and controlled to meet many different desired conditions and applications.

The discussion above generally outlines the connection of connection traces 140 to multi-lumen lead 150. That said, the illustrated connection traces 140 could be challenging to fabricate, and alternative structures may be more efficient. Also, it may be necessary to include additional structures within the multi-lumen lead 150 to achieve the necessary electrical connections. FIGS. 16-24 present several embodiments for the connection mechanisms between the electrical wires from the multi-lumen lead 150 and the thin film substrate 110, which allow electrical stimulation signals to be transferred to related electrodes 120. These connection mechanisms may be referred to as macro-to-micro transitions, where "macro" refers to the wires from the multi-lumen lead, and "micro" refers to the components on the thin film substrate, such as the traces 140, since the dimensions of the wires from the multi-lumen lead 150 are substantially larger than the dimensions of the components on the thin film substrate 110 (e.g., larger by orders of magnitude). For example, a supply wire 510 (discussed below in more detail) coming from the multi-lumen lead 150 may be at least ten times thicker than the trace 140 in the Z-direction, or at least two times wider than the trace 140 (e.g., the width of the supply wire 510 measured in the X-direction versus the width of the trace 140 measured in the Y-direction).

Figure 16A:
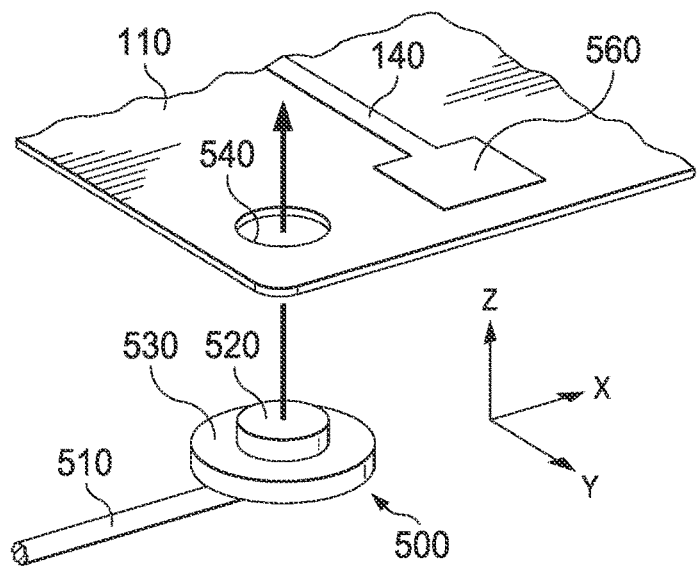
FIGS. 16A-16C are three-dimensional perspective views of a connection structure for a thin film lead assembly according to an embodiment of the present disclosure.
Figure 16B:
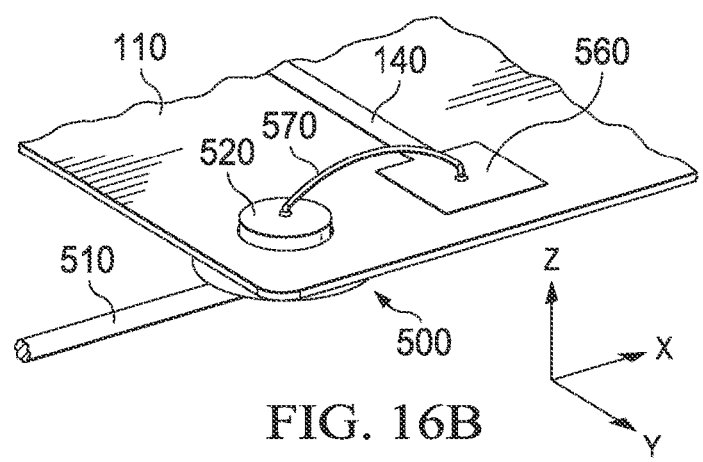
Figure 16C:
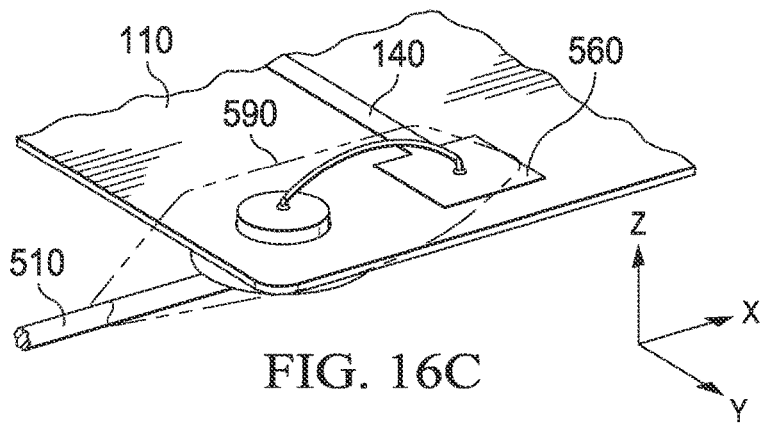

FIGS. 16A-16C illustrate the different steps of mechanically and electrically coupling a "macro" component and a "micro" component according to a first embodiment of the present disclosure. The illustrated connection mechanism uses a transition pad 500 to accommodate an electrical connection between the supply wire 510 and a related signal trace 140. The supply wire 510 may be an embodiment of the connection wire 170 discussed above with reference to FIG. 5. In some embodiments, the transition pad 500 contains platinum. In other embodiments, the transition pad 500 may include other types of conductive materials. The supply wire 510 includes a conductive wire extending from the multi-lumen lead (or from another type of suitable lead structure) in the X-direction. A first end of the supply wire 510 is configured for insertion into a respective lumen 160 in the multi-lumen lead 150, while a second end of the supply wire 510 is configured for bonding or attachment with the micro-component of the lead assembly 100, such as the trace 140, which is a non-limiting example of the signal trace 140 that is implemented on the thin film substrate 110 discussed above. In some embodiments, the supply wire 510 may include a metal alloy, such as a nickel-cobalt base alloy (e.g., MP35N), an alloy with a silver core, or an alloy with a platinum core.

Note that the actual device may have a plurality of supply wires 510, where each supply wire 510 carries electrical signals to a respective one of the electrodes 120, thereby allowing electrical stimulation/sensing to be delivered/sensed by the different electrodes 120 independently. For reasons of simplicity, however, only one supply wire 510 is illustrated herein.

As discussed above, the supply wire 510 may be considered the "macro" component herein, since it is substantially larger than components on the thin film substrate 110, such as the trace 140. The signal trace 140 may be considered the "micro" component, since its size or dimensions are substantially smaller than the supply wire 510.

In this embodiment, the transition pad 500 is configured as a disc-like structure having an extending post 520, which extends upwards from a base 530. In embodiments where the extending post and the base 530 are both circularly shaped, the extending post 520 has a smaller circumference or diameter than the base 530. As part of the electrical circuit, the supply wire 510 is connected to a back or bottom side of the transition pad 500 (e.g., opposite from the extending post 520). Some examples of the actual connection mechanism include soldering or resistance welding. As part of this connection mechanism, an opening 540 is formed as part of the thin film substrate 110, which is sized to receive the extending post 520 but not the base 530 of the transition pad 500. For example, the opening 540 may have a diameter or circumference that is substantially the same as (or just slightly larger than) the diameter or circumference of the extending post 520, respectively, such that the extending post 520 can fit through the opening 540, but the base 530 cannot.

A conductive pad 560 is also implemented on the front or top side of the planar surface of the thin film substrate 110, where the trace 140 terminates. The conductive pad 560 may also be viewed as an extension of the trace 140, but with a larger dimension in the X-direction. In some embodiments, the conductive pad 560 is a platinum pad, but the conductive pad 560 may include other types of conductive materials in other embodiments.

As step 1 of the assembly process illustrated in FIG. 16A, the extending post 520 is inserted through the opening 540. Since the base 530 of the transition pad 500 (i.e., the portion below the extending post 520) is larger than the opening 540, the base 530 of the transition pad 500 does not extend into the opening 540. Rather, the upper surface of the base 530 may come into direct physical contact with a bottom surface of the thin film substrate 110 to ensure that the transition pad 500 is firmly attached to the thin film substrate 110.

As step 2 of the assembly process illustrated in FIG. 16B, the extending post 520 has been inserted through the opening 540 and now protrudes over the top side of planar surface of the thin film substrate 110 in the Z-direction. To provide an electrical signal path, a gold wire bond 570 is attached to both the extending post 520 and the conductive pad 560.

As step 3 of the assembly process illustrated in FIG. 16C, an epoxy encasement 590 is applied to the connection structure (e.g., including the extending post 520, the conductive pad 560, the gold wire bond 570, and at least portions of the supply wire 510) and portions of the planar surface of the thin film substrate 110, so as to provide protection to the connection structure and to isolate the electrical signals involved. In some embodiments, the epoxy encasement 590 may include a conductive epoxy material, for example, an epoxy material that contains silver.

Figure 17A:
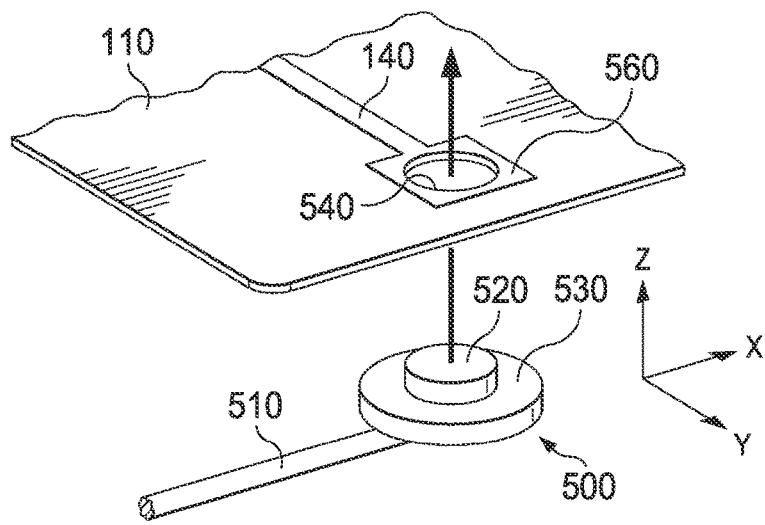
FIGS. 17A-17C are three-dimensional perspective views of a connection structure for a thin film lead assembly according to an embodiment of the present disclosure.
Figure 17B:
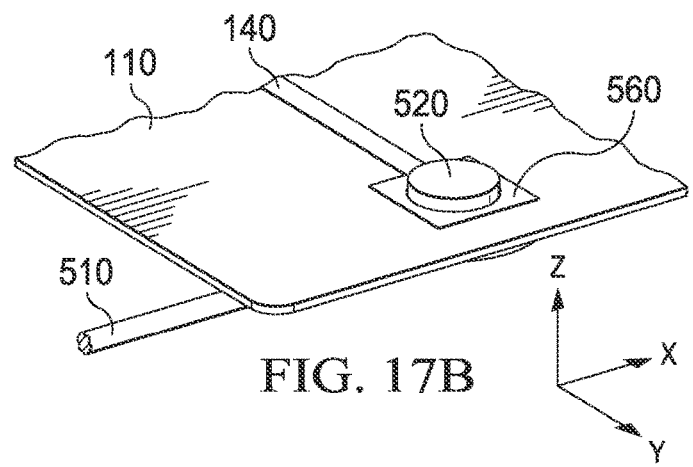
Figure 17C:
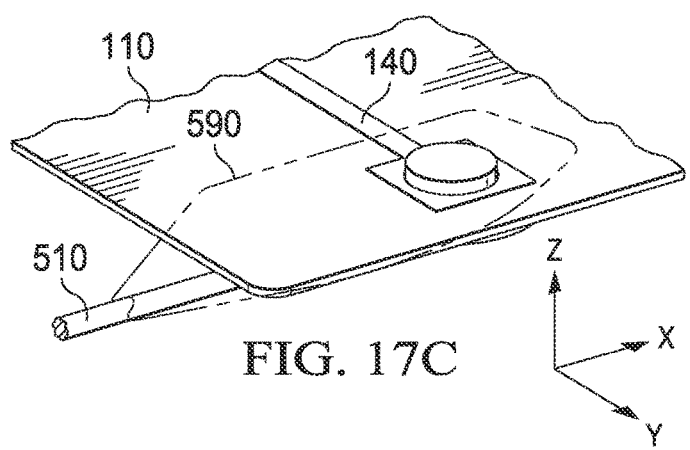

FIGS. 17A-17C illustrate the different steps of mechanically and electrically coupling a "macro" component and a "micro" component according to a second embodiment of the present disclosure. For reasons of consistency and clarity, similar components in FIGS. 16A-16C and 17A-17C will be labeled the same. In step 1 shown in FIG. 17A, the second embodiment also makes use of the transition pad 500 to provide necessary electrical connections between the supply wire 510 and the signal trace 140. Unlike the first embodiment where the opening 540 is formed in the thin film substrate 110 and away from the conductive pad 560, the second embodiment forms the opening 540 in the conductive pad 560 itself. In step 2, the transition pad 500 has its extending post 520 inserted into the opening 540. Again, similar to the first embodiment shown in FIGS. 16A-16C, since the dimensions of the opening 540 are smaller than the dimensions of the base 530 of the transition pad 500, the base 530 does not extend through the opening 540 but rather is secured to the bottom surface of the thin film substrate 110 by pressing against it. A crimp or compression fit can also be utilized to accommodate the connection between conductive pad 560 and the transition pad 500, or make the connection more secure. Alternatively, soldering or conductive epoxy can be used. Alternatively, the opening 540 can be configured as a conductive via, which will allow traditional flow soldering techniques to be used. In step 3, the epoxy encasement 590 is added to surround the electrically connecting components, such as the conductive pad 560 and the extending post 520.

Figure 18A:
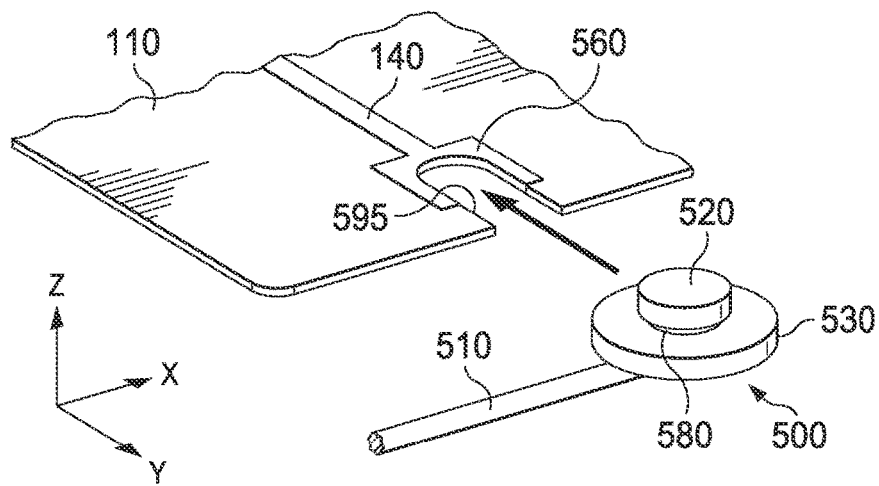
FIGS. 18A-18C are three-dimensional perspective views of a connection structure for a thin film lead assembly according to an embodiment of the present disclosure.
Figure 18B:
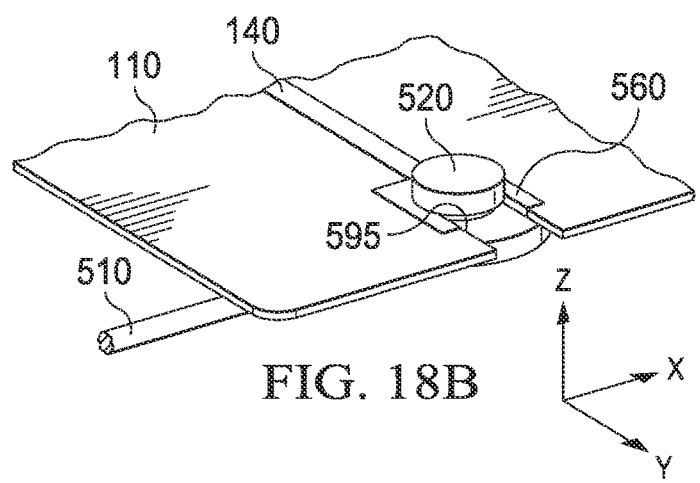
Figure 18C:
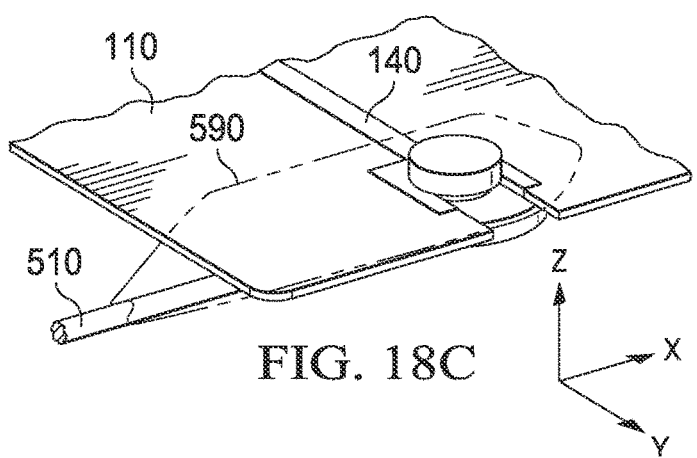

FIGS. 18A-18C illustrate the different steps of mechanically and electrically coupling a "macro" component and a "micro" component according to a third embodiment of the present disclosure. For reasons of consistency and clarity, similar components in FIGS. 16A-16C, FIGS. 17A-17C, and 18A-18C will be labeled the same. In this third embodiment, the transition pad 500 is revised to include a recess 580 (or groove) between the base 530 and the extending post 520. For example, the recess 580 has a smaller circumference than both the extending post 520 and the base 530, such that an outer rim portion of the extending post 520 is separated from the base 530 in the Z-direction. Meanwhile, a slot 595 is cut into the conductive pad 560. The slot 595 may face the Y-direction and is configured to substantially match the dimensions of the recess 580, both in the X-direction and in the Z-direction.

In step 1 shown in FIG. 18A, the third embodiment positions the transition pad 500 adjacent to the slot 595. In step 2 shown in FIG. 18B, the transition pad 500 is slid into the slot 595. Since the slot 595 is smaller (e.g., in the X-direction) than the extending post 520 and the base 530, the conductive pad 560 makes direct physical contact with the bottom surface of the outer rim portion of the extending post 520, and/or with the top surface of the base 530. In step 3 of the third embodiment shown in FIG. 18C, crimping may be performed to further clamp the transition pad 500 with the conductive pad 560. In addition, solder and/or conductive epoxy may be applied between the transition pad 500 and the conductive pad 560 to further ensure their electrical connection. In this manner, the transition pad 500 and the conductive pad 560 may collectively form a conductive via. Lastly, an epoxy encasement 590 is added to surround the electrically connecting components, such as the conductive pad 560 and the extending post 520.

Figure 19:
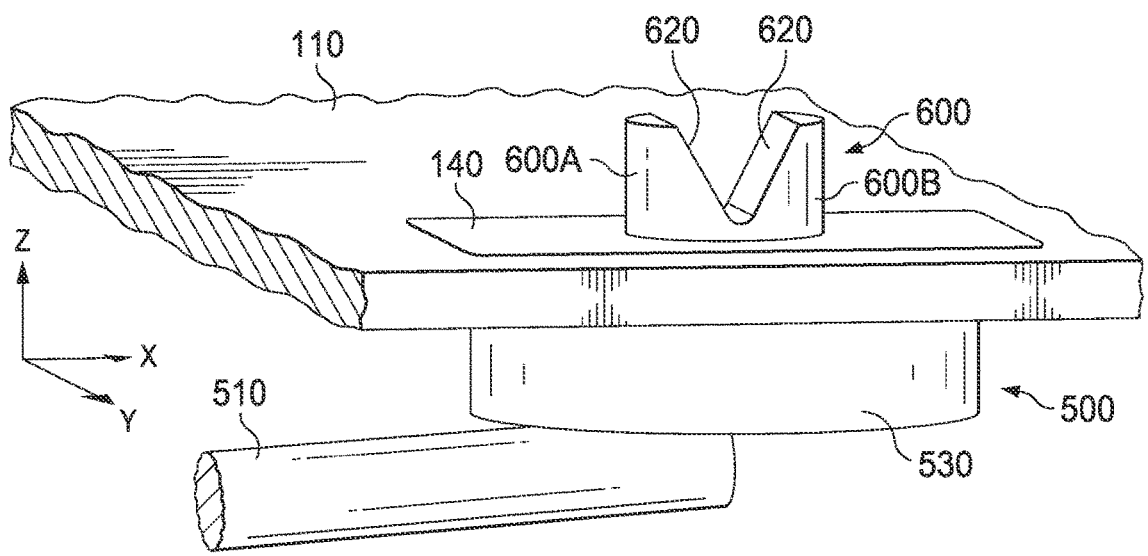
FIG. 19 is a three-dimensional perspective view of a connection structure for a thin film lead assembly according to an embodiment of the present disclosure.

It is understood that although the embodiments illustrated in FIGS. 16A-16C, 17A-17C, and 18A-18C use a circular extending post 520 for the transition pad 500, that is not intended to be limiting. For example, FIG. 19 illustrates a three-dimensional perspective view of another embodiment of the transition pad 500, where a ridged structure 600 is implemented (instead of the circular extending post 520) on top of the base 530 that is connected to the supply wire 510. The ridged structure 600 may be fitted through an opening similar to the opening 540 discussed above and protrudes over the top planar surface of the thin film substrate 110. The ridged structure 600 may include a plurality of ridged segments, such as ridged segments 600A and 600B in the illustrated embodiment. Each of the ridged segments 600A-600B has a flat surface 620, which face each other in the X-direction. The ridged segments 600A and 600B may be crimped down, for example by pressing on the flat surfaces 620, to make physical contact with traces 140. Alternatively, conductive epoxy may be applied over the ridged segments 600A-600B and over the traces 140 to establish the electrical connection between the ridged structure 600 (and therefore the supply wire 510) and the traces 140.

Figure 20A:
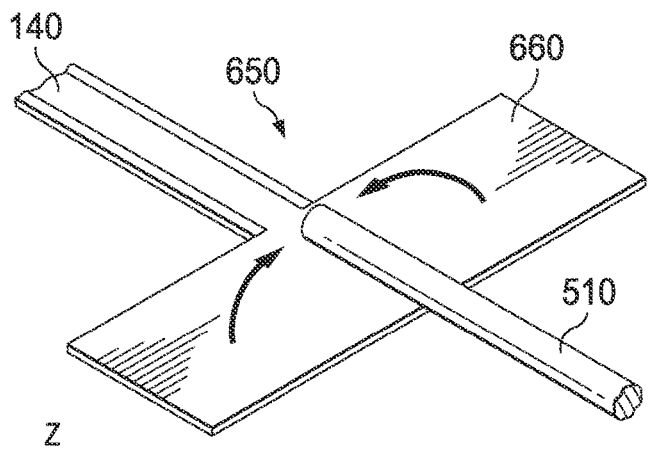
FIGS. 20A-20E are three-dimensional perspective views of connection structures for a thin film lead assembly according to various embodiments of the present disclosure.

FIGS. 20A-20E illustrate the three-dimensional perspective views of several other connection techniques that make use of alternative structures designed into the thin film substrate 110, in order to facilitate the macro-to-micro transition. For example, as shown in FIG. 20A, the thin film substrate 110 may be manufactured to include a T-leg connection 650, which is also made of the same polyimide material as the thin film substrate 110 itself. The T-leg connection 650 includes the trace 140 and a connection pad 660, which is an extension of the conductive trace 140. The connection pad 660 extends laterally away from the trace 140 in the Y-direction. To achieve electrical connection between the supply wire 510 and the T-leg connection 650, both lateral extensions of the connection pad 660 are wrapped around the supply wire 510. For example, a first lateral extension of the connection pad 660 may be wrapped around the supply wire 510, and then the second lateral extension of the connection pad 660 may be wrapped around the first lateral extension of the connection pad 660, which already has the supply wire 510 wrapped therein. The supply wire 510 may be considered a part of the T-leg connection 650. As such, electrical connectivity between the supply wire 510 and the thin film substrate 110 (e.g., a corresponding one of the electrodes 120) may be established.

Figure 20B:
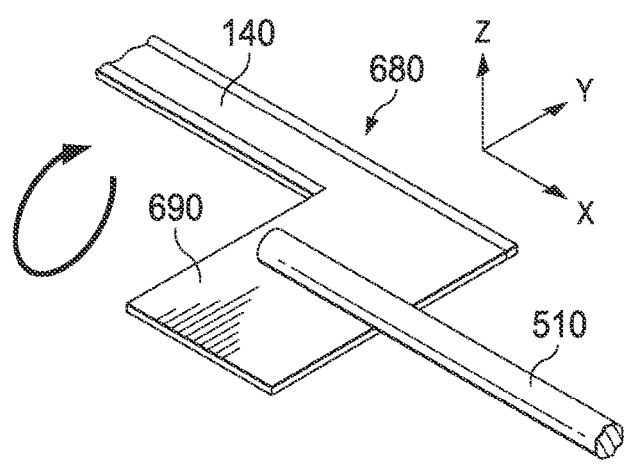

FIG. 20B illustrates an L-leg connection 680, which is also made of the same polyimide material as the thin film substrate 110 itself. The L-leg connection 680 includes the trace 140 and a connection pad 690, which is an extension of the trace 140 and that extends laterally to one side. To achieve electrical connection between the supply wire 510 and the L-leg connection 680, portions of the connection pad 690 are wrapped around the supply wire 510. The supply wire 510 may be considered a part of the L-leg connection 680. As such, electrical connectivity between the supply wire 510 and the thin film substrate 110 (e.g., a corresponding one of the electrodes 120) may be established.

Figure 20C:
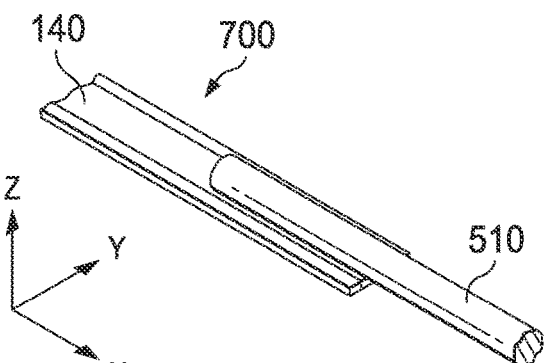

FIG. 20C illustrates an I-leg connection 700, which is also made of the same polyimide material as the thin film substrate 110 itself. The I-leg connection 700 includes the conductive trace 140. In some embodiments, the trace 140 may define a trough or trench, through which the supply wire 510 is inserted in order to achieve electrical connection between the supply wire 510 and the I-leg connection 700. The supply wire 510 may be considered a part of the I-leg connection 700. It is understood that in the T-leg embodiment, the L-leg embodiment, and the I-leg embodiment, welding, soldering, or conductive epoxy may also be used to facilitate the electrical connections. Additionally, crimping mechanisms could also be used.

Figure 20D:
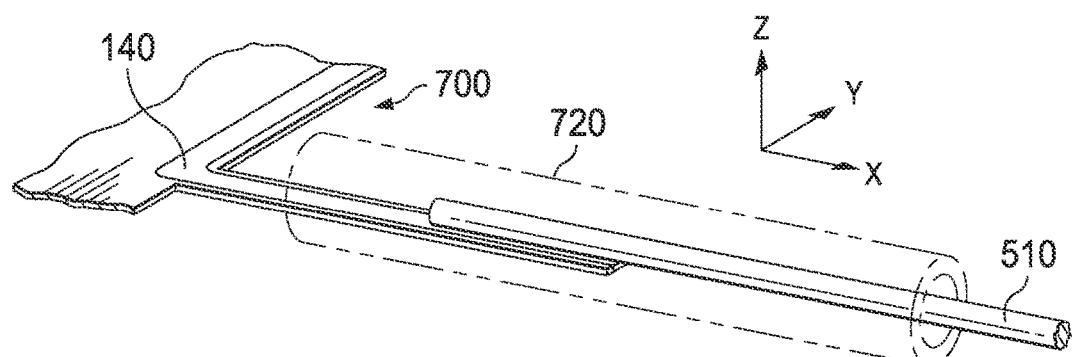
Figure 20E:
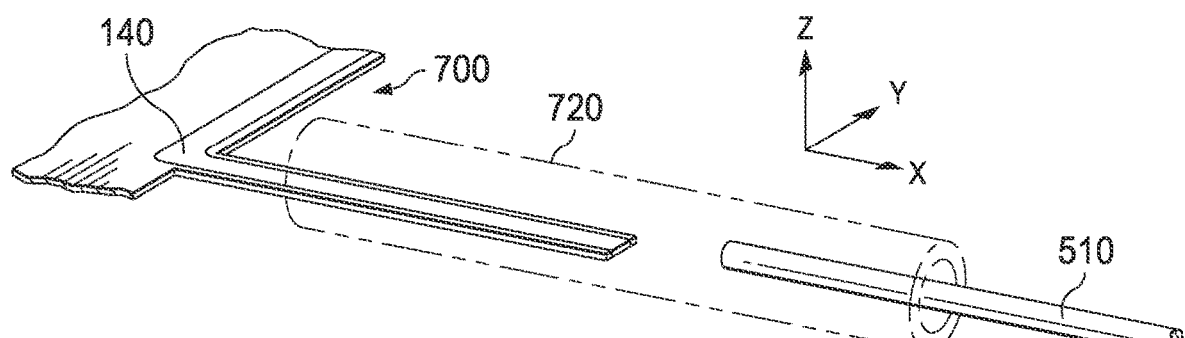

FIGS. 20D and 20E illustrate three-dimensional perspective views of two alternative crimp connection techniques to facilitate the macro-to-micro transition. As shown in FIGS. 20D-20E, a portion of the I-leg connection 700 (which includes the trace 140 and the supply wire 510) is inserted into a sleeve 720. Different materials may be used to implement the sleeve 720 in different embodiments. For example, in some embodiments, the sleeve 720 may be made of polyimide, or another type of electrically insulating material, such as a polymer, silicon, or pellethane material. In other embodiments, the sleeve 720 may be made of a metal material instead. As shown in FIG. 20D, the supply wire 510 may already be in physical contact with the trace 140. In embodiments where the sleeve 720 is made of a metal material, the sleeve 720 may be crimped, so as to establish physical and electrical contact between the sleeve 720, the trace 140, and the supply wire 510. In embodiments where the sleeve 720 is made of the electrically insulating material such as polyimide, the sleeve 720 is not crimped. Rather, a conductive epoxy material may be injected into the sleeve 720 to establish electrical connections between the trace 140 and the supply wire 510 (e.g., since both the trace 140 and the supply wire 510 are in physical and electrical contact with the conductive epoxy injected into the sleeve 720). The sleeve 720 may act as a barrier to hold the conductive epoxy in place and may provide electrical isolation between the different supply wires 510 (associated with different electrodes). As shown in FIG. 20E, the supply wire 510 may be spaced apart from the trace 140. Again, in embodiments where the sleeve 720 is made of metal, the sleeve 720 may be double crimped (one crimp between the sleeve 720 and the trace 140, and another crimp between the sleeve 720 and the supply wire 510) to help establish electrical connections between the supply wire 510 and the trace 140. In embodiments where the sleeve 720 is made of the electrically insulating material such as polyimide, the sleeve 720 is not crimped, and conductive epoxy is injected into the sleeve 720 to help establish electrical connections between the trace 140 and the supply wire 510.

Figure 21A:
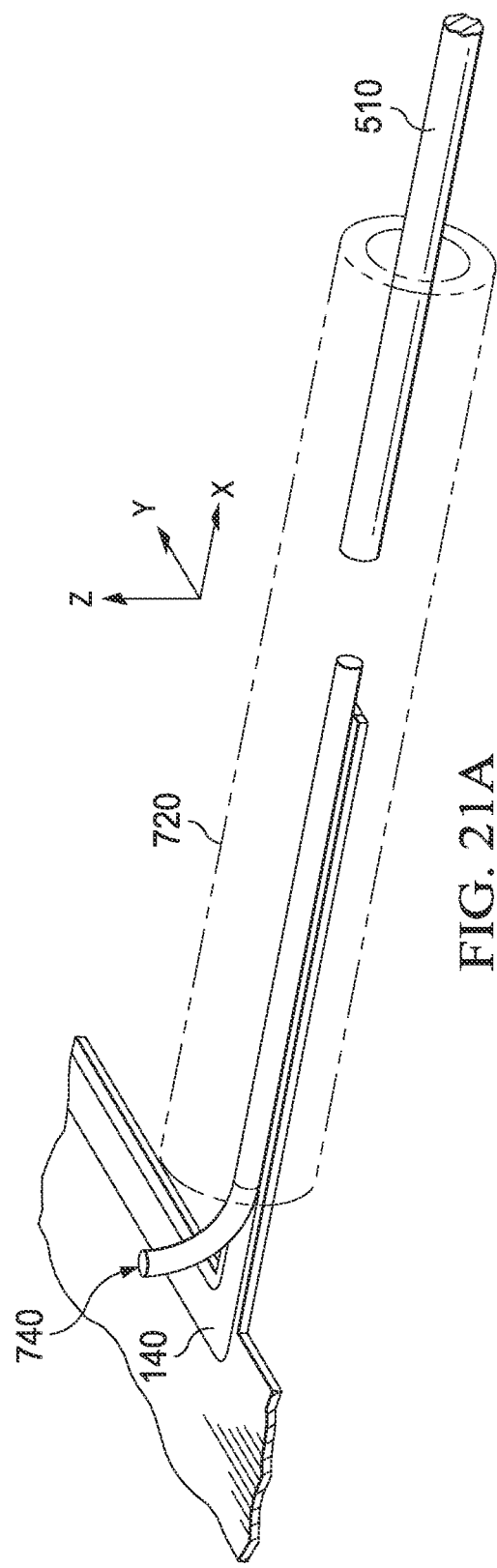
FIGS. 21A-21B are three-dimensional perspective views of connection structures for a thin film lead assembly according to various embodiments of the present disclosure.
Figure 21B:
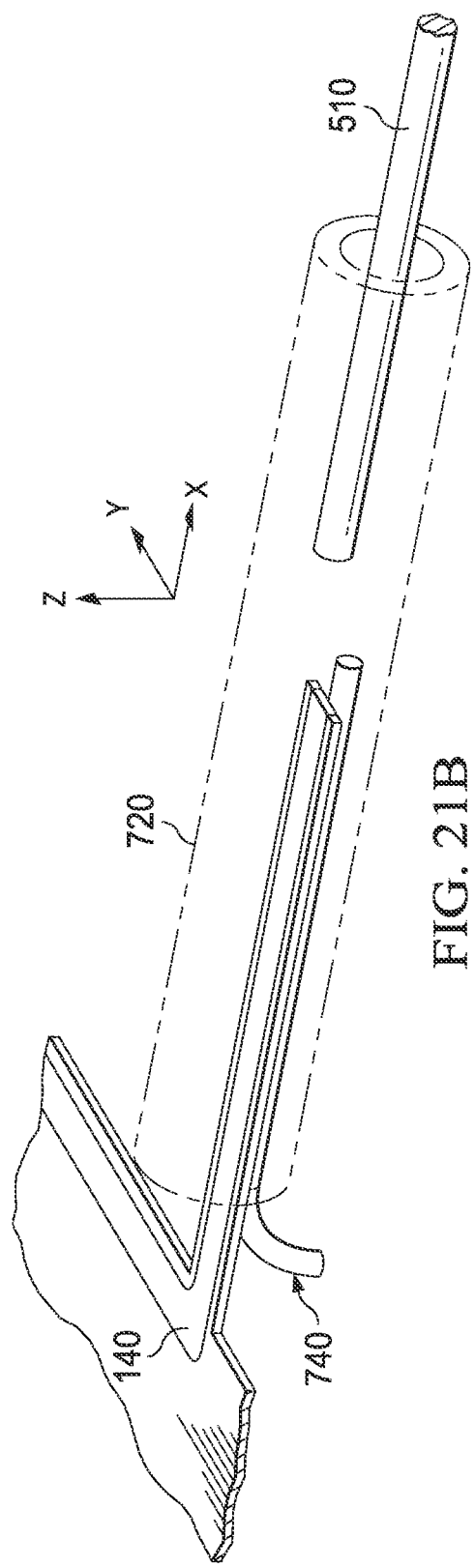

FIGS. 21A and 21B illustrate three-dimensional perspective views of alternative crimp techniques to facilitate the macro-to-micro transition. Similar to the embodiments illustrated in FIG. 20E, a sleeve 720 is provided to house the trace 140 and the supply wire 510 therein. In addition, the embodiments illustrated in FIGS. 21A and 21B may further implement a conductive cable 740 within the sleeve 720. In the embodiment of FIG. 21A, the conductive cable 740 is located on the top surface of the trace 140. In the embodiment of FIG. 21B, the conductive cable 740 is located on the bottom surface of the trace 140. The conductive cable 740 may provide additional electrical connections to other components. In addition, the conductive cable 740 provides additional rigidity, since its presence within the sleeve 720 gives the sleeve 720 another body to grab onto. The sleeve 720 is then double crimped, with a first crimp at the conductive trace within the sleeve 720, and a second crimp at the supply wire 510 within the sleeve 720. As such, the trace 140 (as a part of the thin film substrate 110) is crushed between the conductive cable 740 and the sleeve 720, thereby reinforcing the electrical connection. In the embodiment described above, the sleeve 720 is made of a metal material. It is understood that in alternative embodiments, the sleeve 720 may be made of a non-conductive material such as polyimide, in which case conductive epoxy may be injected into the sleeve 720 to establish the electrical connection between the trace 140, the supply wire 510, and the conductive cable 740, with no crimping involved.

Figure 22:
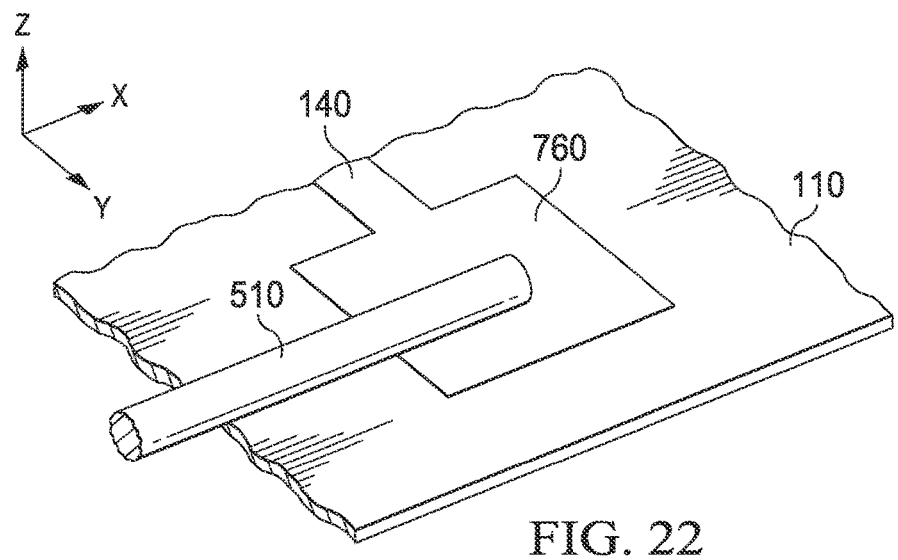
FIG. 22 is a three-dimensional perspective view of connection structures for a thin film lead assembly according to an embodiment of the present disclosure.

FIG. 22 illustrates a three-dimensional perspective view of a connection mechanism to facilitate the macro-to-micro transition according to yet another embodiment of the present disclosure. In this embodiment, the supply wire 510 is bonded to a conductive pad 760. The conductive pad 760 is connected to, or implemented as an extension of, the trace 140. The conductive pad 760 may include platinum, or at least has a platinum surface. In the embodiment illustrated in FIG. 22, the supply wire 510 is directly bonded to the conductive pad 760 using a laser welding process. As the inventors of this present disclosure have recognized, due to the extreme thinness of a typical conductive pad formed on the thin film substrate 110, the energy required to bond the supply wire 510 to the conductive pad 760 directly via the laser welding process would exceed what a conductive pad (that is typically implemented on a thin film substrate 110) can tolerate. In other words, the energy associated with laser welding the supply wire 510 to a typical conductive pad would likely damage the typical conductive pad, thereby degrading its performance or rendering it unusable.

To address this issue, the present disclosure increases the thickness (e.g., in the vertical Z-direction) of the conductive pad 760, before laser welding is performed to bond the supply wire 510 to the conductive pad 760. In some embodiments, an electroplating process is performed to form the conductive pad 760 with an enhanced thickness on the thin film substrate 110, or alternatively, thicken a typical conductive pad that is already formed on the thin film substrate 110. As such, the thickness of the conductive pad 760 is substantially greater than a thickness of the rest of the trace 140. In some embodiments, the thickness of the trace 140 is in a range between about 2.5 microns and about 3 microns, and the thickness of the conductive pad 760 (after electroplating) is in a range between about 50 microns and about 70 microns. With the increased thickness, the conductive pad 760 can now tolerate the energy associated with the laser welding process, thus allowing the supply wire 510 to be directly bonded to the conductive pad 760.

Figure 23A:
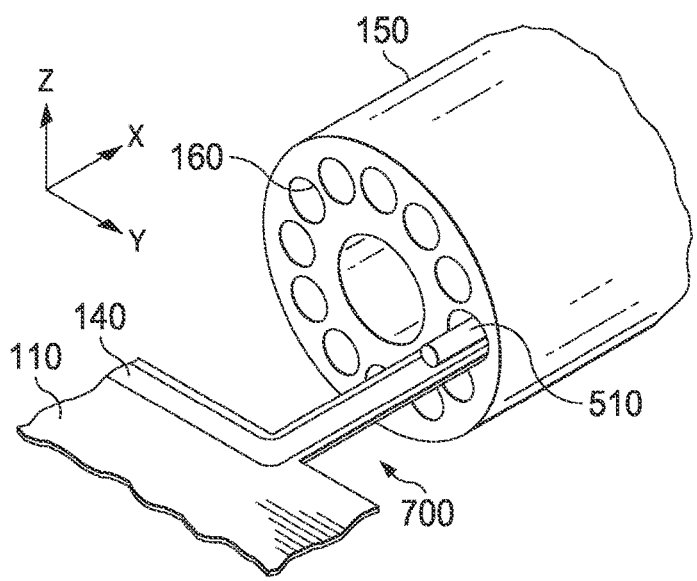
FIGS. 23A-23B are three-dimensional perspective views of connection structures for a thin film lead assembly according to an embodiment of the present disclosure.
Figure 23B:
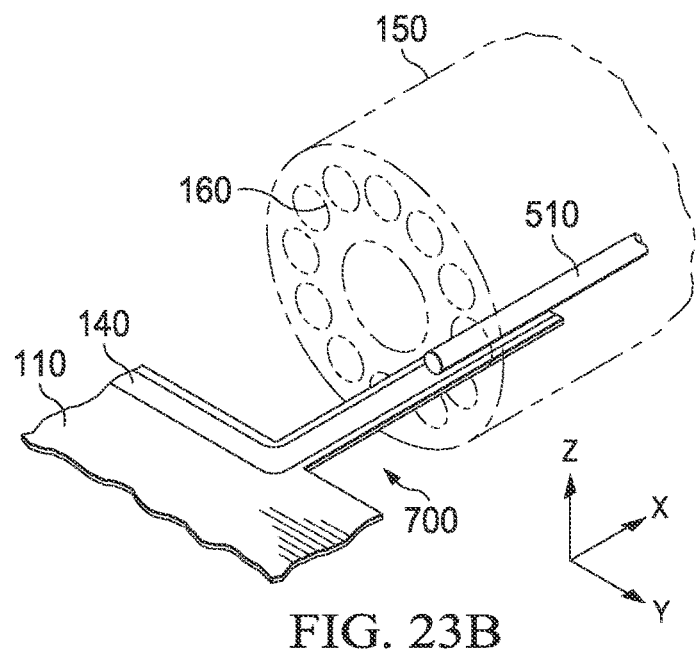

FIGS. 23A-23B illustrate three-dimensional perspective views of another embodiment of a connection mechanism to facilitate the macro-to-micro transition. In more detail, the I-leg connection 700 (as the "micro" component and discussed above with reference to FIG. 20C) is inserted directly to the lumen 160 of the multi-lumen lead 150 (as the "macro" component discussed above with reference to FIG. 5). The electrically insulating material of the multi-lumen lead 150 is illustrated non-transparently in FIG. 23A and transparently in FIG. 23B. The supply wire 510 coming out of each of the lumens is placed on the trace 140 of the corresponding I-leg connection 700 that is inserted into the lumen. The lumen is then backfilled with a conductive epoxy material to lock the I-leg connection 700 in place with the supply wire 510 and to ensure their electrical connection is firmly established. It is understood that a plurality of the I-leg connections 700 may be implemented, for example, one for each of the lumens 160. However, for reasons of simplicity, only one such I-leg connection 700 is shown herein.

Figure 24:
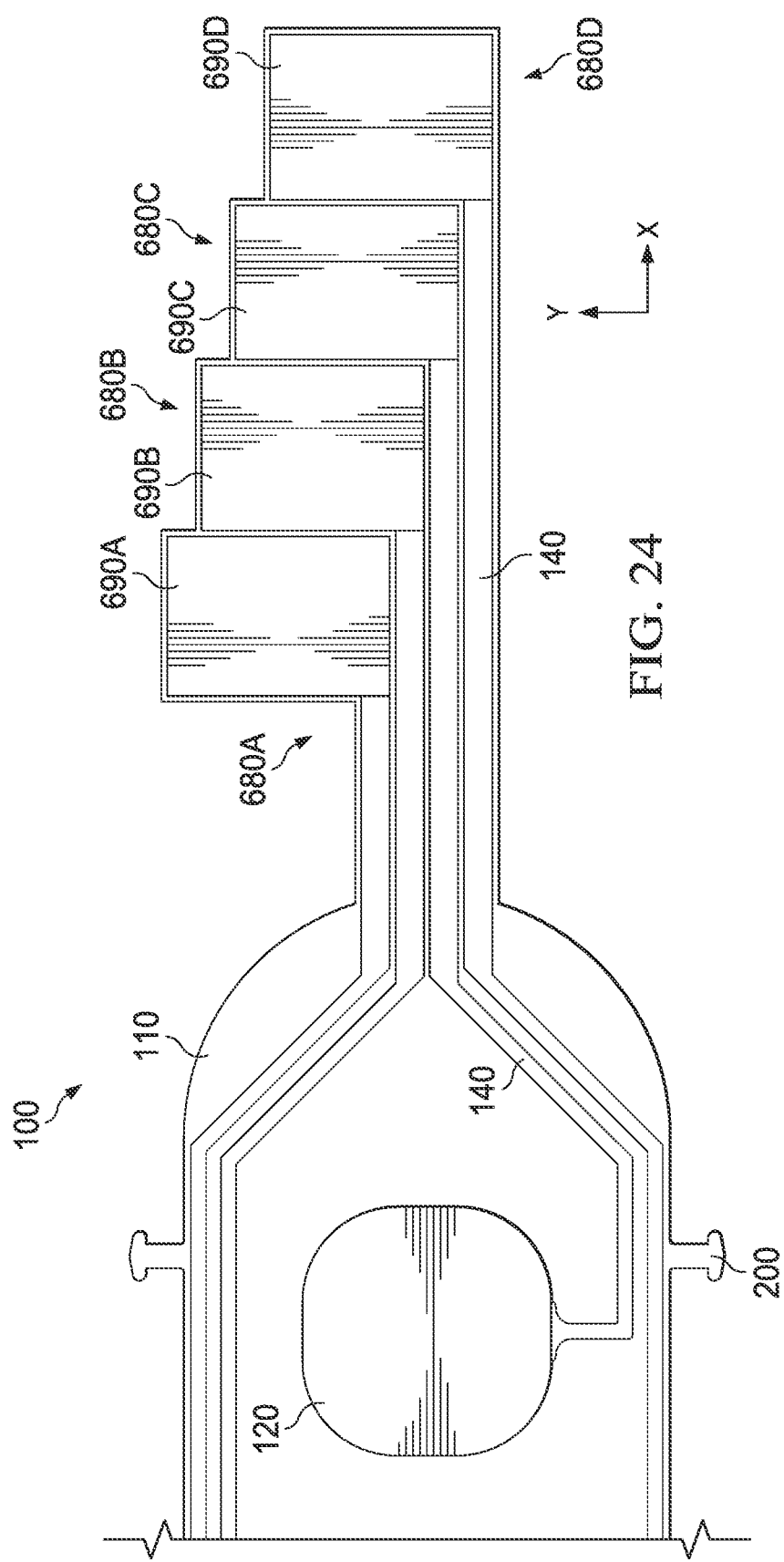
FIG. 24 is a top view of a connection structure for a thin film lead assembly according to an embodiment of the present disclosure.
Figure 25D:
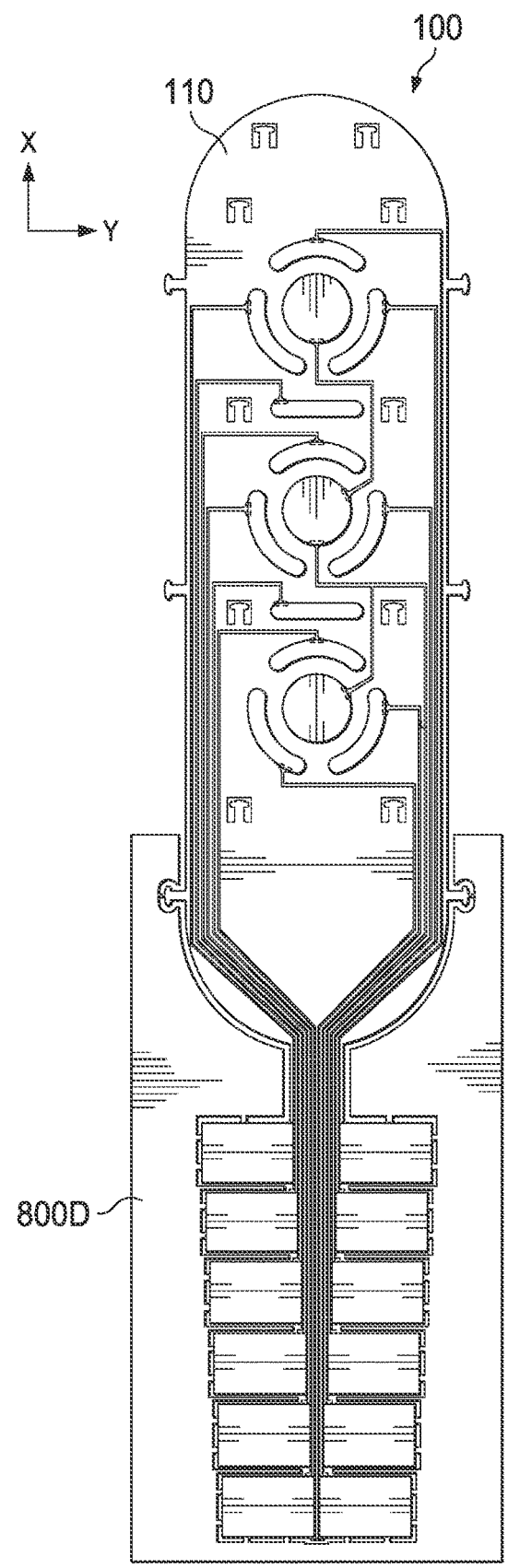

FIG. 24 illustrates a top view of a staggered legs arrangement for the lead assembly 100 on a mask according to an embodiment of the present disclosure. In more detail, the mask may be a lithography mask used in a lithography process to define the shapes and sizes of the various components of the lead assembly 100. Thus, the patterns of the mask shown in FIG. 24 are labeled the same as their corresponding components in the fabricated lead assembly 100.

The embodiment of FIG. 24 implements four instances of the L-leg connection 680 discussed above with reference to FIG. 20B, which are illustrated in FIG. 24 as the L-leg connections 680A, 680B, 680C, and 680D. Each of the L-leg connections 680A-680D includes a respective one of the traces 140 that are routed to the thin film substrate 110. Each of the L-leg connections 680A-680D also includes a respective conductive pad 690A, 690B, 690C, and 690D, that is connected to the respective trace 140. As discussed above, each of the conductive pads 690A-690D may receive a respective supply wire 510 (i.e., the "macro" component) from the multi-lumen lead 150. A conductive epoxy may be applied to the supply wire 510 and the respective conductive pad 690A/B/C/D located below in order to physically and electrically connect them together. It will be recognized that in some alternative embodiments, the conductive pads 690A/B/C/D could also be connected to their respective supply wires 510 using techniques such as crimping, welding, or soldering.

The conductive pads 690A-690D are arranged in a staggered configuration. For example, the conductive pad 690A is located the closest to the thin film substrate 110 in the X-direction and is located "above" the rest of the conductive pads 690B, 690C, and 690D in the Y-direction. The conductive pad 690B is located farther away from the thin film substrate 110 in the X-direction than the conductive pad 690A and is located "below" the conductive pad 690A in the Y-direction, but it is located above the rest of the conductive pads 690C and 690D in the Y-direction. The conductive pad 690C is located farther away from the thin film substrate 110 in the X-direction than the conductive pads 690A-690B and is located "below" the conductive pads 690A-690B in the Y-direction, but it is located above the conductive pad 690D in the Y-direction. The conductive pad 690D is located the farthest away from the thin film substrate 110 in the X-direction and is located "below" all the conductive pads 690A-690C in the Y-direction.

Such a staggered arrangement for the conductive pads 690A-690D helps defer the "bulk" attributed to the "legs" of the L-leg connections (e.g., the "legs" are the conductive pads 690A-690D). Had the conductive pads 690A-690D not been staggered, the spacing between their corresponding traces 140 would have to be significantly widened in the Y-direction, in order to ensure that the conductive pads 690A-690D do not short into each other. But by staggering the conductive pads 690A-690D, the bulk attributed to the conductive pads 690A-690D does not rise very much above just the size (e.g., in the Y-direction) of one of the conductive pads 690A-690D. Consequently, mask space and/or actual device space, which may be valuable, may be conserved by the staggered L-leg connections shown in FIG. 24.

In some embodiments, an assembly fixture is used to align the staggered conductive pads 690A/B/C/D, so that the supply wires 510 can be attached thereto using conductive epoxy. FIGS. 25A-25E illustrate top views several embodiments of such assembly fixtures 800A, 800B, 800C, and 800D. The assembly fixtures 800A (shown in FIG. 25A) and 800C (shown in FIG. 25C) each surrounds an entirety of the thin film lead assembly 100 in the top view, whereas the assembly fixtures 800B (shown in FIG. 25B) and 800D (shown in FIG. 25D) each surrounds a portion of the thin film lead assembly 100 in the top view. The assembly fixtures 800A-800D reduce the complexity or difficulty in handling the traces 140, for example, the "legs" of the T-leg. L-leg, or I-leg connections discussed above.

In more detail, due to the fact that the traces 140 are thin, narrow, and light in weight, they could curl up or down (e.g., in the Z-direction), or otherwise flop around and potentially get entangled with one another after the thin film lead assembly 100 is taken out of a box or a tray. This makes the handling of the thin film lead assembly 100 more difficult. Furthermore, the curling/flopping/entanglement of the traces 140 may potentially damage or the trace or degrade its electrical performance. Unfortunately, conventional thin film leads have not devised a satisfactory solution to this problem.

The present disclosure overcomes the problems discussed above by implementing the assembly fixtures 800A-800D that help secure the traces 140 in place until the traces are ready for bonding (e.g., with the other connection mechanisms discussed above). For example, the assembly fixtures 800A-800D are fabricated from the same material (e.g., polyimide) as the thin film substrate 110. In other words, the assembly fixtures 800A-800D and the thin film substrate 110 come from the same sheet of thin film substrate material, and their respective outlines or contours are defined by a laser cut process subsequently. However, such a laser cut process is specifically configured to leave "bridges" 820 (labeled and shown more clearly in the magnified view of a bottom portion of the thin film lead assembly 100 in FIG. 25E) that connect the assembly fixtures 800A-800D to their respective thin film substrates 110. The bridges 820 are portions of the thin film substrate material (e.g., polyimide) that are not cut or etched and that are remain between the thin film substrate 110 and the assembly fixtures 800A-800D after the laser cut process. Through these bridges 820, the assembly fixtures 800A-800D can weigh down, or hold planar, the portions of the thin film substrate 110 on which the conductive pads (such as the conductive pads 690A-690D discussed above with reference to FIG. 24) will be formed. And since these portions of the thin film substrate 110 are tied to respective ones of the traces 140, the traces 140 are also weighed down or held planar via the bridges 820 to the assembly fixtures 800A-800D. When the traces 140 are ready to be bonded to the connection mechanisms discussed above, the bridges 820 may be removed, for example, using a scalpel, a knife, a blade, or another suitable cutting mechanism. The removal of the bridges 820 then free up the corresponding trace 140 for attachment with other structures, such as the connection mechanisms discussed above. In some embodiments, the bridges 820 are removed one at a time, so that the associated trace 140 may be bonded to a suitable connection mechanism before the next bridge 820 is removed. In this manner, the assembly fixtures 800A-800D can effectively prevent the undesirable curling, flopping, or entanglement of the traces 140.

Figure 26A:
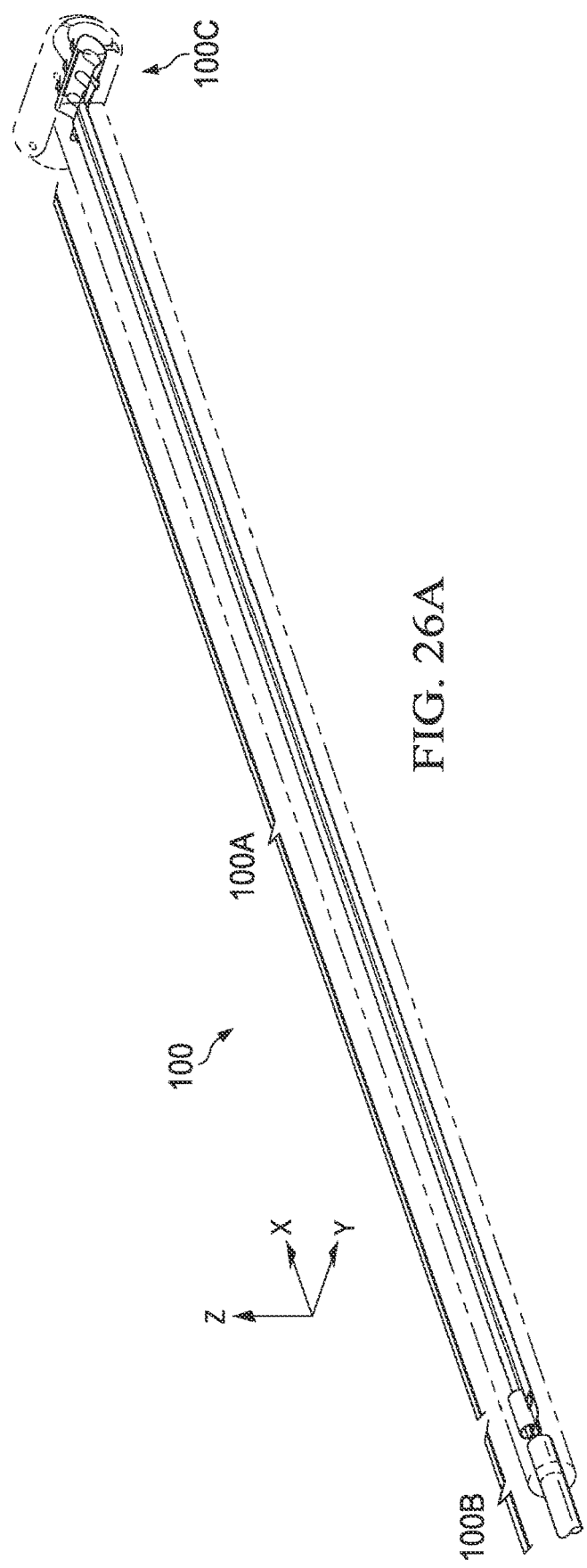
Figure 26B:
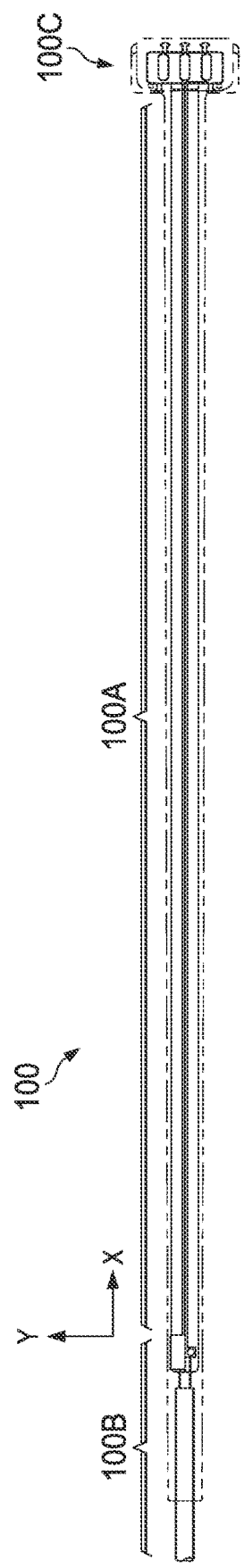

FIGS. 26A-26C illustrate perspective, top, and side views of the thin film lead assembly 100, respectively, according to another embodiment of the present disclosure. This embodiment of the thin film lead assembly 100 is a cuff lead, similar to the cuff lead illustrated in FIGS. 11-15. However, compared to the embodiment of the cuff lead in FIGS. 11-15, the embodiment of the cuff lead in FIGS. 26A-26C has a substantially longer body portion 100A. In that regard, the thin film lead assembly 100 includes the body portion 100A, a macro-to-micro transition portion 100B, and a therapy-delivery portion 100C. The macro-to-micro transition portion 100B may refer to the various embodiments of mechanisms that are discussed above in association with FIGS. 16-24. In other words, the macro-to-micro transition portion 100B is where the conductors from the multi-lumen lead are connected to the conductors (e.g., the traces) of the thin film lead assembly 100. The therapy-delivery portion 100C may refer to the portion of the thin film assembly 100 containing the electrodes, as well as the attachment structures discussed above in association with FIGS. 1-15. Via the electrodes, the therapy-delivery portion 100C may apply electrical stimulation therapy to a target issue of a patient's body, for example, to a peripheral nerve, a spinal cord, or a pelvic nerve or a pudendal nerve.

The body portion 100A connects the macro-to-micro transition portion 100B to the therapy-delivery portion 100C, and it may include a thin film substrate and a trace implemented thereon. The substantially greater dimension (in the X-direction) of the body portion 100A herein may offer certain advantages. For example, the macro-to-micro transition portion 100B may be bulky. If the body portion 100A is too short, the macro-to-micro transition portion 100B would be implemented very close to the therapy-delivery portion 100C. Such a close proximity between the macro-to-micro transition portion 100B and the therapy-delivery portion 100C may exert excessive pressure on the therapy-delivery portion 100C, which in turn exerts undue pressure to the target nerve tissue. This may degrade the efficacy of the electrical stimulation therapy or cause patient discomfort, which is undesirable. Here, by implementing a long body portion 100A, the bulk associated with the macro-to-micro transition portion 100B is deferred away from the therapy-delivery portion 100C. As such, even if the macro-to-micro transition portion 100B is bulky, the amount of pressure it exerts to the therapy-delivery portion 100C (and thus to the target nerve tissue) may be negligible. Therefore, the efficacy of the electrical stimulation therapy may be substantially improved.

In some embodiments, the length of the body portion 100A shown in FIGS. 26A-26C may be in a range between about 1 inch and about 6 inches, for example, between about 4 inches and about 6 inches in some embodiments. In comparison, the length of the corresponding body portion in the embodiment shown in FIGS. 11-15 may be in a range between about ¼ inch and about 1 inch. As such, it can be seen that the body portion 100A herein is substantially longer (e.g., multiple times longer) than the corresponding body portion in a similar thin film lead assembly. Another metric of describing the "long" thin film lead assembly 100 of the embodiment of FIGS. 26A-26C is via a ratio between the length of body portion 100A and the length of the therapy-delivery portion 100C. In some embodiments, the ratio between the length of body portion 100A and the length of the therapy-delivery portion 100C (both measured in the X-direction) is in a range between about 10:1 and about 30:1. In other words, the body portion 100A may be 10 times to 30 times longer than the therapy-delivery portion 100C. It is understood that these numerical ranges are not randomly chosen but rather are specifically configured to optimize performance. If the body portion 100A is too short, the bulk of the macro-to-micro transition portion 100B would not be sufficiently deferred away from the therapy-delivery portion 100C, and the target nerve tissue may still experience too much undue pressure from the macro-to-micro transition portion 100A. On the other hand, if the body portion 100A is too long, it may lead to not only a waste of materials (to implement such a long lead), but also an increased difficulty in fabricating and/or handling the thin film lead assembly 100. By configuring the length of the body portion 100A to be within the ranges described above, the present disclosure ensures that the "bulk" can be adequately deferred in order to reduce the undue pressure on the target nerves, while still making the fabrication and handling of the thin film lead assembly 100 sufficiently simple. It is understood that these ranges may be customized for a specific patient. In other words, depending on the specific anatomy of the patient, different dimensions and/or ranges may be configured to optimize the therapeutic efficacy.

In some embodiments, different amounts of silicone may be applied to the body portion 100A and the therapy-delivery portion 100C. For example, instead of applying equal amounts of silicone (or another type of molding material that provides rigidity to the structure of the thin film lead assembly 100) to both the body portion 100A and the therapy-delivery portion 100C, the present disclosure may apply a thinner layer of silicone to the body portion 100A and a thicker layer of silicone to the therapy-delivery portion 100C. The thinner layer of silicone for the body portion 100A may provide more flexibility to the body portion 100A and reduce the amount of pressure it may exert against the therapy-delivery portion 100C, and thus also reduce the pressure load against the target nerve tissue.

It is understood that although FIGS. 26A-26C illustrate a cuff lead as an embodiment of the "long body" embodiment of the thin film lead assembly 100, the "long body" concept may apply to other types of thin film lead assemblies as well, for example to planar paddle thin film lead assemblies.

FIG. 27 is a flowchart illustrating a method 1000 of fabricating a thin film lead assembly. The method 1000 includes a step 1010 to provide a thin film substrate having a plurality of electrodes disposed thereon. The electrodes are exposed from a front side of the thin film substrate. The thin film substrate contains polyimide or another suitable type of thin film material and includes a plurality of tabs that extend outwards.

The method 1000 includes a step 1020 to fold each of the tabs toward a back side of the thin film substrate.

The method 1000 includes a step 1030 to apply a molding material to the back side of the thin film substrate. The molding material encases each of the tabs therein, thereby promoting adhesion between the thin film substrate and the molding material.

In some embodiments, the step 1010 comprises fabricating the thin film substrate and the tabs simultaneously at least in part via one or more lithography processes, wherein the tabs are fabricated as integral parts of the thin film substrate.

FIG. 28 is a flowchart illustrating a method 1100 of implementing a macro-to-micro connection for a thin film lead assembly. The method 1100 includes a step 1110 to provide a thin film substrate having an electrode and a trace disposed thereon. The electrode is connected to the trace, and wherein the thin film substrate contains polyimide or another suitable type of thin film material.

The method 1100 includes a step 1120 to provide a supply wire that is substantially larger than the trace. A first end of the supply wire is configured for insertion into a lumen of a multi-lumen lead.

The method 1100 includes a step 1130 to couple a second end of the supply wire to the trace via a coupling structure.

In some embodiments, the coupling structure includes a transition pad having a base and an extending post. The step 1130 may further include the following steps: forming an opening in the thin film substrate; maneuvering the transition pad partially through the opening such that the extending post is disposed above the thin film substrate and the base is disposed below the thin film substrate; and attaching the extending post to the trace via wire bonding or via direct physical contact.

In some embodiments, the step 1130 may include the following steps: performing electroplating to increase a thickness of a conductive pad on the thin film substrate, wherein the conductive pad is connected to the trace; and laser welding the second end of the supply wire to the conductive pad after the electroplating.

In some embodiments, the coupling structure includes a T-leg connection structure or an L-leg connection structure that each have a connection pad that extends laterally outwards. The step 1130 may include wrapping the connection pad around the supply wire.

In some embodiments, the coupling structure includes a polyimide tube and an I-leg connection structure. The step 1130 may include the following steps: inserting the supply wire and the I-leg connection structure into the polyimide tube, and filling the polyimide tube with a conductive epoxy.

In some embodiments, the coupling structure further includes a conductive wire. The step 1130 may further include the inserting the conductive wire into the polyimide tube such that the conductive wire is located between the I-leg connection structure and the polyimide tube.

The devices and methods implemented in the manner described in the present disclosure may offer advantages over conventional devices and methods. However, it is understood that not all advantages are discussed herein, different embodiments may offer different advantages, and that no particular advantage is required for any embodiment. One advantage is that the attachment structures (e.g., the T-shaped attachment structures 200 and 210 discussed above) may enhance adhesion between the thin film substrate and a molding material such as silicone. Instead of relying on just the adhesion between a planar surface of a thin film substrate and silicone to prevent potential delamination, the attachment structures of the present disclosure offer additional connection points for the silicone material. For example, the attachment structures may extend into the silicone, and their encasement in the silicone makes it more difficult for the thin film substrate to be pulled off of the silicone, or vice versa. As a result, the likelihood of delamination between the thin film substrate and the silicone is substantially reduced. Another advantage is a feasible macro-to-micro transition. Since the sizes and dimensions of the macro component (e.g., the supply wire from the lumen) are so much larger than the traces on the thin film substrate, it is typically very difficult to establish a connection between them without damaging some of the components involved. The present disclosure overcomes this problem by implementing a plurality of feasible structures that could each be used to facilitate such a macro-to-micro transition. For example, the macro-to-micro coupling structures may include transition pads and/or bond wires, T-leg/L-leg/I-leg connections, sleeves/tubes filled with conductive epoxy, staggered arrangements of L-legs, etc. Another advantage is that the fixture discussed above helps weigh down the traces to facilitate the manipulation and handling of the thin film leads. Other advantages include low costs and ease of implementation.

One aspect of the present disclosure involves an apparatus. The apparatus includes an elongate thin film body extending from a first end to a second end. The apparatus includes a plurality of electrodes disposed on the thin film body. The apparatus includes a plurality of electrode connection traces that are each coupled to a respective one of the electrodes. The apparatus includes a plurality of attachment structures placed at predetermined locations about the thin film body. The apparatus includes an outer molding surrounding the thin film body, the attachment structures providing connection points for the outer molding, thus allowing for adhesion between the outer molding and the thin film body.

Another aspect of the present disclosure involves an apparatus. The apparatus includes a substrate that contains polyimide or another suitable type of thin film material. The apparatus includes a plurality of electrodes disposed on the substrate, wherein the electrodes are configured to deliver electrical stimulation to nerve issue located on a first side of the substrate. The apparatus includes a molding material disposed on a second side of the substrate opposite the first side, wherein the disposition of the molding material on the substrate provides rigidity to the substrate. The apparatus includes a plurality of attachment structures disposed on the substrate, wherein the attachment structures each protrude into, and are surrounded by, the molding material on the second side.

Yet another aspect of the present disclosure involves a method. The method includes providing a thin film substrate having an electrode and a trace disposed thereon, wherein the electrode is connected to the trace, and wherein the thin film substrate contains polyimide or another suitable type of thin film material. The method includes providing a supply wire that is substantially larger than the trace, wherein a first end of the supply wire is configured for insertion into a lumen of a multi-lumen lead. The method includes coupling a second end of the supply wire to the trace via a coupling structure.

Yet another aspect of the present disclosure involves a lead assembly. The lead assembly includes a thin film body supporting a plurality of stimulation electrodes, wherein the thin film body includes a polyimide substrate or another suitable type of thin film substrate. The lead assembly includes a plurality of electrode connection traces situated on the thin film body and electrically connected to respective ones of the plurality of stimulation electrodes. The lead assembly includes a connection wire configured to provide stimulation signals for transmission to the plurality of stimulation electrodes, wherein the connection wire extends from a lumen of a multi-lumen lead and is substantially larger than each of the electrode connection traces. The lead assembly includes a coupling structure configured to provide electrical connection between the connection wire and the electrode connection traces.

Yet another aspect of the present disclosure involves a lead assembly. The lead assembly includes a polyimide substrate or another suitable type of thin film substrate. The lead assembly includes an electrode and a connection trace situated on the polyimide substrate, wherein the electrode is connected to the connection trace. The lead assembly includes a supply wire extending from a lumen of a multi-lumen lead, wherein the supply wire is substantially larger than the connection trace. The lead assembly includes a coupling structure configured to mechanically and electrically couple the electrode and the connection trace together.

Yet another aspect of the present disclosure involves a method. The method includes providing a thin film substrate having an electrode and a trace disposed thereon, wherein the electrode is connected to the trace, and wherein the thin film substrate contains polyimide. The method includes providing a supply wire that is substantially larger than the trace, wherein a first end of the supply wire is configured for insertion into a lumen of a multi-lumen lead. The method includes coupling a second end of the supply wire to the trace via a coupling structure.

Various embodiments of the invention have been described above for purposes of illustrating the details thereof and to enable one of ordinary skill in the art to make and use the invention. The details and features of the disclosed embodiment [s] are not intended to be limiting, as many variations and modifications will be readily apparent to those of skill in the art. Accordingly, the scope of the present disclosure is intended to be interpreted broadly and to include all variations and modifications coming within the scope and spirit of the appended claims and their legal equivalents.

The invention claimed is:

1. A lead assembly, comprising:
   a thin film body supporting a plurality of electrodes, wherein the thin film body includes a substrate;
   a plurality of electrode connection traces situated on the thin film body and electrically connected to respective ones of the plurality of electrodes;
   a connection wire configured to provide electrical signals for transmission to the plurality of electrodes, wherein the connection wire extends from a lumen of a lead and is substantially larger than each of the electrode connection traces; and
   a coupling structure configured to provide electrical connection between the connection wire and the electrode connection traces, wherein a first portion of the coupling structure is disposed over a first side of the substrate, and wherein a second portion of the coupling structure is disposed over a second side of the substrate opposite the first side;
   wherein the coupling structure includes:
   a transition pad that is connected to the connection wire;
   a conductive pad that is connected to one of the electrode connection traces; and
   a bonding wire that is bonded to both the transition pad and the conductive pad.

2. The lead assembly of claim 1, wherein:
   the thin film body includes a substrate having an opening;
   the transition pad includes a base and an extending post that is located over the base;
   the extending post is disposed through the opening and protrudes over the substrate;
   the base is disposed below the substrate; and the bonding wire is bonded to the extending post.

3. The lead assembly of claim 1, wherein the coupling structure further includes an epoxy material that is disposed on the conductive pad, at least a portion of the transition pad, and the bonding wire.

4. The lead assembly of claim 1, wherein the coupling structure includes:
   a conductive pad that is connected to one of the electrode connection traces, the conductive pad containing an opening;
   a transition pad that is connected to the connection wire, the transition pad including a base and an extending post located on the base, wherein the extending post extends through the opening and protrudes over the thin film body; and an epoxy material that is located on the conductive pad and the extending post.

5. The lead assembly of claim 4, wherein:
the opening is configured as a slot that opens to a side; and
the transition pad includes a recess between the extending post and the base, the recess being configured to match the slot, such that the recess of the transition pad can be slid into the slot from the side.

6. The lead assembly of claim 1, wherein the coupling structure includes a T-leg connection, an L-leg connection, or an I-leg connection each configured to receive the connection wire.

7. The lead assembly of claim 6, wherein:
the coupling structure includes the I-leg connection;
the lead includes a multi-lumen lead;
the I-leg connection is directly inserted into a lumen of the multi-lumen lead; and the lumen is filled with a conductive epoxy.

8. The lead assembly of claim 6, wherein:
the coupling structure includes a plurality of L-leg connections; and the plurality of L-leg connections are arranged in a staggered configuration.

9. The lead assembly of claim 1, wherein the coupling structure includes a tube surrounding the connection wire and a portion of the thin film body containing connection traces.

10. The lead assembly of claim 9, wherein the tube is made of polyimide or a metal material.

11. The lead assembly of claim 1, wherein the coupling structure includes a platinum pad that is laser welded to the connection wire, and wherein the platinum pad is connected to one of the electrode connection traces and is thicker than said electrode connection trace.

12. A lead assembly, comprising:
a thin film substrate;
an electrode and a connection trace situated on the thin film substrate, wherein the electrode is connected to the connection trace;
a supply wire extending from a lumen lead, wherein the supply wire is substantially larger than the connection trace, wherein the supply wire is disposed over a first side of the thin film substrate; and
a coupling structure configured to mechanically and electrically couple the electrode and the connection trace together, wherein a portion of the coupling structure is disposed over a second side of the thin film substrate opposite the first side;
wherein the coupling structure includes:
a transition pad that is connected to the supply wire;
a conductive pad that is connected to one of the connection traces; and
a bonding wire that is bonded to both the transition pad and the conductive pad.

13. The lead assembly of claim 12, wherein the coupling structure includes a T-leg connection, an L-leg connection, or an I-leg connection each configured to receive the supply wire.

14. A lead assembly, comprising:
a substrate that contains polyimide, wherein the substrate has a planar surface spanning in a first horizontal direction and a second horizontal direction;
a plurality of electrodes located on the substrate;
a plurality of electrode connection traces situated on the substrate and electrically connected to the plurality of electrodes, respectively;
a connection wire configured to provide electrical signals for transmission to the plurality of electrodes; and
a coupling structure configured to provide electrical connection between the connection wire and the electrode connection traces, wherein the coupling structure includes a transition pad that is connected to the connection wire, a conductive pad that is connected to one of the electrode connection traces, and a bonding wire that is bonded to both the transition pad and the conductive pad, and wherein the transition pad and the conductive pad are locationally offset with respect to one another in at least one of the first horizontal direction or the second horizontal direction.

15. The lead assembly of claim 14, wherein:
the substrate includes an opening;
the transition pad includes a base and an extending post that is located over the base;
the extending post is disposed through the opening and protrudes over the substrate;
the base is disposed below the substrate; and the bonding wire is bonded to the extending post.

16. The lead assembly of claim 14, wherein the coupling structure further includes an epoxy material that is disposed on the conductive pad, on at least a portion of the transition pad, or on the bonding wire.

17. The lead assembly of claim 14, wherein the coupling structure includes a T-leg connection configured to receive the connection wire.

18. The lead assembly of claim 14, wherein the coupling structure includes a tube surrounding the connection wire and a portion of the substrate containing the electrode connection traces.

19. The lead assembly of claim 18, wherein the tube contains polyimide.

20. The lead assembly of claim 12, wherein:
the thin film substrate has an opening;
the transition pad includes a base and an extending post that is located over the base;
the extending post is disposed through the opening and protrudes over the substrate;
the base is disposed below the substrate; and
the bonding wire is bonded to the extending post.

* * * * *

UNITED STATES PATENT AND TRADEMARK OFFICE
CERTIFICATE OF CORRECTION

PATENT NO. : 12,226,637 B2  
APPLICATION NO. : 17/212283  
DATED : February 18, 2025  
INVENTOR(S) : Todd Hanson et al.

Page 1 of 1

It is certified that error appears in the above-identified patent and that said Letters Patent is hereby corrected as shown below:

In the Specification

Column 3, Line 55, change "case" to -- ease --

Signed and Sealed this
Tenth Day of June, 2025

Coke Morgan Stewart
*Acting Director of the United States Patent and Trademark Office*